Figure 1:
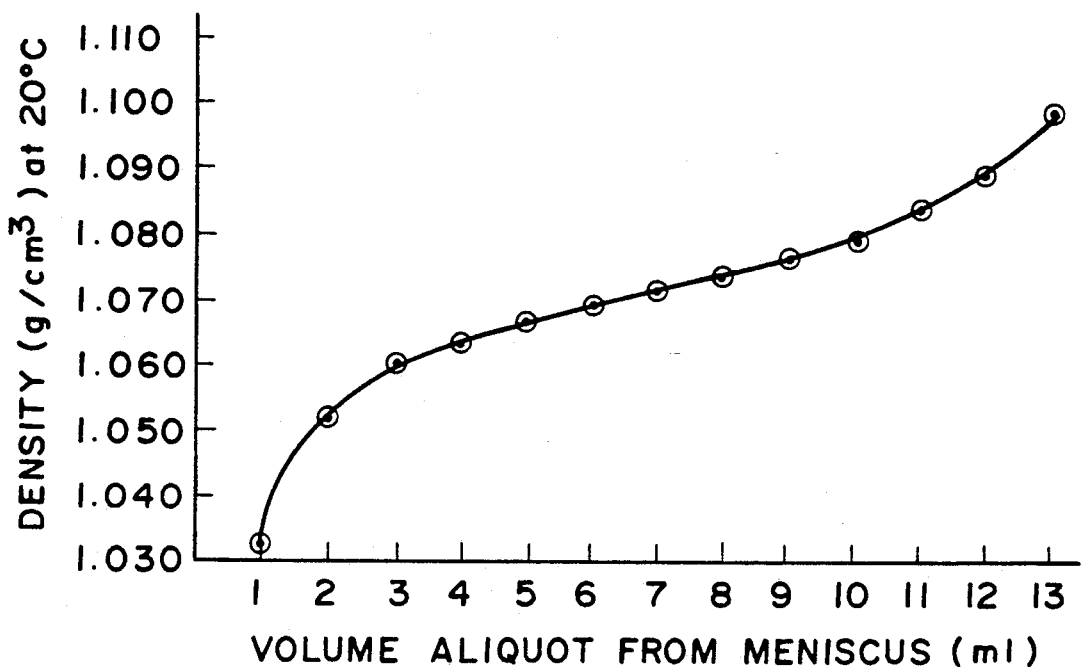

United States Patent [19]

Cercek et al.

[11] Patent Number: 5,260,186
[45] Date of Patent: Nov. 9, 1993

[54] PROVISION OF DENSITY SPECIFIC BLOOD CELLS FOR THE STRUCTUREDNESS OF THE CYTOPLASMIC MATRIX (SCM) TEST

[76] Inventors: Boris Cercek; Lea Cercek, both of 4318 Camphor Ave., Yorba Linda, Calif. 92686

[21] Appl. No.: 716,755

[22] Filed: Jun. 18, 1991

Related U.S. Application Data

[63] Continuation of Ser. No. 260,928, Oct. 21, 1988, abandoned, which is a continuation-in-part of Ser. No. 838,264, Mar. 10, 1986, abandoned.

[51] Int. Cl.$^5$ .......................... C12Q 1/02; C12Q 1/24; G01N 33/567; G01N 33/569
[52] U.S. Cl. .......................................... 435/2; 435/5; 435/7.23; 435/7.24; 435/7.32; 435/29; 435/30; 435/243; 436/63; 436/64; 436/503; 436/805; 436/811; 436/813; 436/827
[58] Field of Search ...................... 435/2, 5, 7.23, 7.24, 435/7.32, 29, 30, 243; 436/63, 64, 503, 811, 813, 827, 805

[56] References Cited

U.S. PATENT DOCUMENTS 4,190,535 2/1980 Luderer et al.
4,835,103 5/1989 Cercek et al. ........................ 436/63

FOREIGN PATENT DOCUMENTS 0190488 8/1986 European Pat. Off.
WO86/03007 5/1986 PCT Int'l Appl.
WO87/05393 9/1987 PCT Int'l Appl.
WO87/07382 12/1987 PCT Int'l Appl.

OTHER PUBLICATIONS

K. Shortman, "Analytical and Preparative Equilibrium Density Separation of Lymphoid Cells on Albumin and Metrizamide," in *Methods of Enzymology: Immunological Techniques Part G—Separation and Characterization of Lymphoid Cells* (G. Di Sabato, et al., eds., Academic Press, New York, 1984), pp. 102–117.

J. Matsumoto, T. Tenzaki & T. Ishiguro, "Clinical Evaluation of Fluorescein Polarization of Peripheral Lymphocytes (SCM Test) in the Diagnosis of Cancer," *J. Japan Soc. Cancer Ther.* 20, 728–734 (1985).

L. Cercek, B. Cercek, & C. I. V. Franklin, "Biophysical Differentiation Between Lymphocytes from Healthy Donors, Patients with Malignant Diseases and Other Disorders," *Brit. J. Cancer* 29, 345–352 (1974).

L. Cercek & B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977).

L. Cercek & B. Cercek, "Effects of Osmolality and Density of Gradients on the Isolation of SCM-Responding Lymphocytes," *Brit. J. Cancer* 38, 163–165 (1978).

(List continued on next page.)

*Primary Examiner*—David Saunders
*Attorney, Agent, or Firm*—Sheldon & Mak

[57] ABSTRACT

An improved method is provided for the isolation of lymphocytes for use in the SCM test for the detection of cancer and other diseases and conditions. The method of the present invention can isolate either or both of the SCM-responding lymphocyte fractions from the same blood sample: the F2 fraction, with a buoyant density of 1.0590 g/cm$^3$ to 1.0670 g/cm$^3$ measured at 20° C. in a solution having an osmolality of about 0.315 Osm/kg, and the F4 fraction, with a buoyant density of 1.0690 g/cm$^3$ to 1.0730 g/cm$^3$. These lymphocyte fractions are isolated in visible bands and are substantially free of lymphocytes having other buoyant densities. This avoids cross-contamination of the lymphocyte fractions with each other as well as with SCM non-responding lymphocytes. Several gradients useful in this isolation method are described. This isolation method can use as starting material either a blood sample depleted of phagocytic cells or the total population of lymphocytes. The latter avoids the use of iron powder or carbonyl-iron powder in removing the phagocytic cells.

81 Claims, 1 Drawing Sheet

OTHER PUBLICATIONS

L. Cercek & B. Cercek, "Apparent Tumour Specificity with the SCM Test," *Brit. J. Cancer* 31, 252–253 (1975).

R. J. Atkinson, W. S. Lowry, & P. Strain, "An Analysis of the SCM Test in Cancer Diagnosis," *Cancer* 52, 91–100 (1983).

J. A. V. Pritchard, J. E. Seaman, I. H. Evans, K. W. James, W. H. Sutherland, T. J. Deeley, I. J. Kerby, & I. C. M. Patterson, "Cancer-Specific Density Changes in Lymphocytes After Stimulation with Phytohaemagglutinin," *Lancet* 11, 1275–1277 (Dec. 16, 1978).

J. A. V. Pritchard, W. H. Sutherland, J. G. Siddall, A. J. Bater, I. J. Kerby, T. J. Deeley, G. Griffith, R. Sinclair, B. H. Davies, A. Rimmer, & D. J. T. Webster, "A Clinical Assessment of Fluorescence Polarisation Changes in Lymphocytes Stimulated by Phytohaemagglutinin (PHA) in Malignant and Benign Diseases," *Eur. J.Cancer, Clin. Oncol.* 18, 651–659 (1982).

W. J. Herbert, P. C. Wilkinson, & D. I. Stott, "Dictionary of Immunology," 3d ed. Blackwell (1985), pp. 15–16.

G. R. Hocking, J. M. Rolland, R. C. Nairn, E. Pihl, A. M. Cuthbertson, E. S. R. Hughes, & W. R. Johnson, "Lymphocyte Fluorescence Polarization Changes After Phytohaemagglutinin Stimulation in the Diagnosis of Colorectal Carcinoma," JNCI 68, 579–583 (1982).

J. M. Rolland, R. C. Nairn, A. P. Nind, & E. Pihl, "Significance of Lymphocyte Fluorescence Polarization Changes After Phytohaemagglutinin Stimulation in Cancer and Noncancer Conditions," *JNCI* 72, 267–273 (1984).

J. A. V. Pritchard & W. H. Sutherland, "Lymphocyte Response to Antigen Stimulation as Measured by Fluorescence Polarization (SCM Test)," *Brit. J. Cancer* 38, 339–343 (1978).

L. Cercek, P. Milenkovic, B. Cercek, & L. G. Lajtha, "Induction of PHA Response in Mouse Bone Marrow Cells by Thymic Extracts as Studied by Changes in the Structuredness of Cytoplasmic Matrix," *Immunology* 29, 885–891 (1975).

L. Cercek & B. Cercek, "Changes in the Structuredness of Cytoplasmic Matrix (SCM) Induced in Mixed Lymphocyte Interactions," *Radiation & Environmental Biophysics* 13, 71–74 (1976).

PROVISION OF DENSITY SPECIFIC BLOOD CELLS FOR THE STRUCTUREDNESS OF THE CYTOPLASMIC MATRIX (SCM) TEST

CROSS-REFERENCE

This application is a continuation of U.S. application Ser. No. 260,928, filed Oct. 21, 1988 and now abandoned, which is a continuation-in-part application of U.S. application Ser. No. 838,264 by Dr. Boris Cercek and Dr. Lea Cercek, filed Mar. 10, 1986 (now abandoned) and also entitled "Provision of Density Specific Blood Cells for the Structuredness of the Cytoplasmic Matrix (SCM) Test," incorporated herein by this reference.

BACKGROUND

This application discloses improved methods for isolating SCM-responding lymphocytes for the performance of the SCM test useful in the detection of cancer and other diseases and conditions.

Many diseases occurring in humans and animals can be detected by the presence of foreign substances, particularly in the blood, which are specifically associated with a disease or condition. Tests for antigens or other such substances produced as a result of such diseases show great promise as a diagnostic tool for the early detection and treatment of the particular disease that produced the antigen or other substance. Procedures for the detection of such substances must be reliable, reproducible, and sensitive in order to constitute a practical diagnostic procedure for health care providers. In addition any such procedure should be able to be carried out by persons of ordinary skill and training in laboratory procedure, and should be relatively fast and inexpensive.

For example, in the treatment of the various malignancies that afflict humans and animals, referred to generally as cancer, it is recognized that early detection is a key to effective treatment, especially as many therapeutic procedures are effective only in relatively early stages of the disease. In fact, virtually all known cancer treatments are not only more effective, but safer, when administered in early stages of cancer. Far too many cases of cancer are only discovered too late for effective treatment.

Accordingly, there is a great need for rapid, easy-to-perform, and reliable tests which can diagnose cancer at early stages. In this connection, new tests and procedures are being developed to effect early diagnosis of the cancer.

We have developed and reported one such test for the early detection of cancer in L. Cercek, B. Cercek, and C. I. V. Franklin, "Biophysical Differentiation Between Lymphocytes from Healthy Donors, Patients with Malignant Disease and Other Disorders," *Brit. J. Cancer* 29, 345-352 (1974) and L. Cercek and B. Cercek, "Application of the Phenomenon of Changes in the Structuredness of Cytoplasmic Matrix (SCM) in the Diagnosis of Malignant Disorders: a Review", *Europ. J. Cancer* 13, 903-915 (1977), which are incorporated herein by this reference.

Our basic SCM test includes the steps of:

(1) challenging a selected subpopulation of lymphocytes from a donor with a challenging agent such as a mitogen or an antigen associated with a condition or disease, such as cancer; and (2) determining the change in structuredness of the cytoplasmic matrix SCM) of the challenged lymphocytes, typically using fluorescence polarization.

SCM reflects the forces of interaction between macromolecules of the cell and other cellular components such as water molecules, ions, adenosine triphosphate, and cyclic adenosine phosphate. Perturbations of these interactions result in changes in SCM.

When applied to cancer, our SCM test is based on the phenomenon that the internal structure of a selected subpopulation of the lymphocytes from a healthy individual is altered when challenged by a mitogen such as phytohaemagglutinin, but is not altered by other selected challenging agents, such as cancer basic protein (CaBP) and/or antigens derived from specific malignant tumors such as tumor associated antigens (TAAs). Contrarily, the equivalent subpopulation of lymphocytes from an individual with cancer responds oppositely. In other words the same subpopulation of lymphocytes from cancer patients does not respond in the SCM test when challenged by a mitogen, but does respond when challenged by a number of cancer-associated antigens. When TAAs derived from specific malignant tumors are used as challenging agents, only lymphocytes from individuals with the same type of tumor from which the TAA had been isolated will respond in the SCM test.

The changes seen in SCM are believed to reflect changes in the internal structure of the lymphocyte as the lymphocyte is activated for synthesis Similar changes can occur in living cells other than lymphocytes during the cell cycle and growth of the cells. Such changes can also be evoked by various external agents, such as ionizing radiation, mechanical forces, chemicals, growth inhibiting and stimulating agents, etc. These changes can be conveniently monitored with a specially adapted technique of fluorescein fluorescence polarization, as we have published in numerous articles, including L. Cercek and B. Cercek, "Studies on the Structuredness of Cytoplasm and Rates of Enzymatic Hydrolysis in Growing Yeast Cells. I. Changes Induced by Ionizing Radiation," *Int. J. Radiat. Biol.* 21, 445-453 (1972); L. Cercek and B. Cercek, "Studies on the Structuredness of Cytoplasm and Rates of Enzymatic Hydrolysis in Growing Yeast Cells. II. Changes Induced by Ultra-Violet Light," *Int. J. Radiat. Biol.* 22, 539-544 (1972); L. Cercek and B. Cercek, "Relationship Between Changes in the Structuredness of Cytoplasm and Rate Constants for the Hydrolysis of FDA in *Saccharomyces cerevisiae*," *Biophysik* 9, 109-112 (1973); L. Cercek, B. Cercek, and C. H. Ockey, "Structuredness of the Cytoplasmic Matrix and Michaelis-Menten Constants for the Hydrolysis of FDA During the Cell Cycle in Chinese Hamster Ovary Cells," *Biophysik* 10, 187-194 (1973); B. I. Lord, L. Cercek, B. Cercek, G. P. Shah, T. M. Dexter and L. G. Lajtha, "Inhibitors of Haemopoietic Cell Proliferation: Specificity of Action Within the Haemopoietic System," *Brit. J. Cancer* 29, 168-175 (1974); L. Cercek and B. Cercek, "Involvement of Cyclic-AMP in Changes of the Structuredness of Cytoplasmic Matrix," *Radiat. & Environ. Biophys.* 11, 209-212 (1974); L. Cercek, P. Milenkovic, B. Cercek, & L. G. Lajtha, "Induction of PHA Response in Mouse Bone Marrow Cells by Thymic Extracts as Studied by Changes in the Structuredness of Cytoplasmic Matrix," *Immunology* 29, 885≧891 (1975); L. Cercek and B. Cercek, "Effects of Osmomolarity, Calcium and Magnesium Ions on the Structuredness of Cytoplasmic Matrix SCM)," *Radiat. & Environ. Biophys.* 13, 9–12 (1976); L. Cercek & B. Cercek, "Changes in the Structuredness of Cytoplasmic Matrix (SCM) Induced in Mixed Lymphocyte Reactions," *Radiat & Environ Biophys.* 13, 71–74 (1976); L. Cercek, B. Cercek, & C. H. Ockey, "Fluorescein Excitation and Emission Polarization Spectra in Living Cells: Changes During the Cell Cycle," *Biophys J.* 23, 395–405 (1978); L. Cercek and B. Cercek, "Effect of Osmolality and Density of Gradients on the Isolation of SCM-Responding Lymphocytes," *Brit. J. Cancer* 38, 163–165 (1978); L. Cercek and B. Cercek, "Involvement of Mitochondria in Changes of Fluorescein Excitation and Emission Polarization Spectra in Living Cells," *Biophys J.* 28, 403–412 (1979); L. Cercek, B. Cercek, and B. I. Lord, "The Effect of Specific Growth Inhibitors on Fluorescein Fluorescence Polarization Spectra in Haemopoietic Cells," *Brit. J. Cancer.* 44, 749–752 (1981); and L. Cercek and B. Cercek, "Effects of Ascorbate Ions on Intracellular Fluorescein Emission Polarization Spectra in Cancer and Normal Proliferating Cells," *Cancer Detection and Prevention* 10, 1–20 (1987), all of which are incorporated herein by this reference.

The usefulness of this SCM test for the detection of cancer has been documented in numerous articles. Articles from our laboratory include; L. Cercek, B. Cercek, and J. V. Garrett, "Biophysical Differentiation Between Normal Human and Chronic Lymphocytic Leukaemia Lymphocytes," in *Lymphocyte Recognition and Effector Mechanisms* (K. Lindahl-Kiessling and D. Osoba eds., New York, Academic Press, 1974), pp. 553–558; L. Cercek, B. Cercek and C. I. V. Franklin, "Biophysical Differentiation between Lymphocytes from Healthy Donors, Patients with Malignant Disease and Other Disorders," *Brit. J. Cancer* 29, 345–352 (1974); L. Cercek and B. Cercek, "Changes in the SCM Response Ratio ($RR_{SCM}$)) After Surgical Removal of Malignant Tissue," *Brit. J. Cancer* 31, 250–251 (1975); L. Cercek and B. Cercek, "Apparent Tumour Specificity with the SCM Test," *Brit. J. Cancer* 31, 252–253 (1975); L. Cercek and B. Cercek, "Changes in the Structuredness of Cytoplasmic Matrix of Lymphocytes as a Diagnostic and Prognostic Test for Cancer," in *Cell Biology and Tumour Immunology, Excerpta Medica International Congress Series No. 349, Proceedings of the XI International Cancer Congress, Florence,* 1974 (Amsterdam, Excerpta Medica, 1974), vol. 1, pp. 318–323; L. Cercek and B. Cercek, "Application of the Phenomenon of Changes in the Structuredness of Cytoplasmic Matrix (SCM) in the Diagnosis of Malignant Disorders: a Review," *Europ. J. Cancer* 13, 903–915 (1977); L. Cercek and B. Cercek, "Detection of Malignant Diseases by Changes in the Structuredness of Cytoplasmic Matrix of Lymphocytes Induced by Phytohaemagglutinin and Cancer Basic Proteins," in *Tumour Markers, Determination and Clinical Role: Proceedings of the Sixth Tenovus Workshop, Cardiff, April* 1977 (K. Griffith, A. M. Neville, and C. G. Pierrepoint, eds., Cardiff, Alpha Omega Publishing Co., (1978), pp. 215–226) and L. Cercek and B. Cercek, "Changes in SCM-Responses of Lymphocytes in Mice After Implantation with Ehrlich Ascites Cells," *Europ. J. Cancer* 17, 167–171 (1981), all of which are incorporated herein by this reference.

The usefulness of the SCM test has been confirmed in articles from other laboratories, including F. Takaku, K. Yamanaka, and Y. Hashimoto, "Usefulness of the SCM Test in the Diagnosis of Gastric Cancer," *Brit. J. Cancer* 36, 810–813 (1977); H. Kreutzmann, T. M. Fliedner, H. J. Galla, and E. Sackmann, "Fluorescence-Polarization Changes in Mononuclear Blood Leucocytes After PHA Incubation: Differences in Cells from Patients with and Without Neoplasia," *Brit. J. Cancer* 37, 797–805 (1978); Y. Hashimoto, T Yamanaka, and F. Takaku, "Differentiation Between Patients with Malignant Diseases and Non-Malignant Diseases or Healthy Donors by Changes of Fluorescence Polarization in the Cytoplasm of Circulating Lymphocytes," *Gann* 69, 145–149 (1978); J. A. V. Pritchard and W. H. Sutherland, "Lymphocyte Response to Antigen Stimulation as Measured by Fluorescence Polarization (SCM-Test)," *Brit. J. Cancer* 38 339–343 (1978); J. A. V. Pritchard, J. E. Seaman, I. H. Evans, K. W. James, W. H. Sutherland, T. J. Deeley, I. J. Kerby, I. C. M. Patterson, and B. H. Davies, "Cancer-Specific Density Changes in Lymphocytes Following Stimulation with Phytohaemagglutinin," *Lancet* 11, 1275–1277 (Dec. 16, 1978); H. Orjasaeter, G. Jordfald, and I. Svendsen, "Response of T-Lymphocytes to Phytohaemagglutinin (PHA) and to Cancer-Tissue-Associated Antigens, Measured by the Intracellular Fluorescence Polarization Technique (SCM Test)," *Brit. J. Cancer* 40, 628–633 (1979); N. D. Schnuda, "Evaluation of Fluorescence Polarization of Human Blood Lymphocytes (SCM Test) in the Diagnosis of Cancer," *Cancer* 46, 1164–1173 (1980); J. A. V. Pritchard, W. H. Sutherland, J. E. Siddall, A. J. Bater, I. J. Kerby, T. J. Deeley, G. Griffith, R. Sinclair, B. H. Davies, A. Rimmer, & D. J. T. Webster, "A Clinical Assessment of Fluorescence Polarisation Changes in Lymphocytes Stimulated by Phytohaemagglutinin (PHA) in Malignant and Benign Disease," *Europ. J. Cancer, Clin. Oncol.* 18,651–659 (1982); G. R. Hocking, J. M. Rolland, R. C. Nairn, E. Pihl, A. M. Cuthbertson, E. S. R Hughes, and W. R. Johnson, "Lymphocyte Fluorescence Polarization Changes After Phytohaemagglutinin Stimulation in the Diagnosis of Colorectal Carcinoma," *J. National Cancer Inst.* 68, 579–583 (1982); M. Deutsch and A. Weinreb, "Validation of the SCM-Test for the Diagnosis of Cancer," *Eur. J. Cancer, Clin. Oncol.* 19, 187–193 (1983); S. Chaitchik, O. Asher, M. Deutsch, and A. Weinreb, "Tumour Specificity of the SCM Test for Cancer Diagnosis," *Europ. J. Cancer, Clin. Oncol.* 21, 1165–1170 (1985); and J. Matsumoto, T. Tenzaki and T. Ishiguro, "Clinical Evaluation of Fluorescein Polarization of Peripheral Lymphocytes (SCM Test) in the Diagnosis of Cancer," *J. Japan Soc. Cancer Ther.* 20, 728–734 (1985), all of which are incorporated herein by this reference.

As reported, the SCM test indicates usefulness both as a screening test for the general detection of malignancies and as a test to diagnose specific types of malignancies. This has been confirmed by blind clinical tests and corroborated by other investigators.

The SCM test can be applied to detection of diseases and conditions other than cancer, such as viral and bacterial infections, including the detection of the AIDS virus, determination of allergic reactions, tissue typing, and monitoring of allograft rejections such as organ transplant rejection based on the SCM responses in mixed lymphocyte reactions, as disclosed in the 1976 *Radiation and Environmental Biophysics* article by L. Cercek and B. Cercek. The presence of other antigen-producing diseases and bodily conditions does not interfere with the SCM test; a patient afflicted with more than one type of antigen-producing disease can be tested for a multiplicity of such diseases simply by running separate tests using for each test an antigen derived from each separate disease or condition being tested for.

When fluorescence polarization is used to determine changes of SCM, such changes are seen as a decrease in the fluorescence polarization of the cells when polarized light is used to excite an intrinsic fluor generated intracellularly by the hydrolysis of a non-fluorescent compound which has been absorbed by the lymphocytes. The fluor typically is fluorescein and the non-fluorogenic compound is typically fluorescein diacetate (FDA). The FDA serves as a fluorogenic agent precursor. An extrinsic fluor is used because the intrinsic fluorescence of cellular components is too small to give meaningful results in this test. Therefore, all references to fluorescence polarization values herein are references to fluorescence polarization values obtained with an extrinsic fluor, preferably one generated by enzymatic hydrolysis from a non-fluorogenic compound added to and absorbed by the cells. Typically, excitation of the fluor occurs with light at 470 nm and the intracellular fluorescein fluorescence polarization peak occurs at 510 nm. Excitation at 442 nm can also be used, in which case the intracellular fluorescein polarization peak occurs at 527 nm.

Intracellular fluorescence polarization is a measure of resistance to rotational relaxation of fluorescein molecules; the greater the intracellular resistance to rotation, the greater the measured fluorescence polarization. As seen in the SCM test, a decrease in fluorescence polarization is believed to result mainly from changes in the conformation of the mitochondria, the energy-producing organelles of the cell. Changes in the mitochondria are believed to result from the contractions of the cristae or inner folds of the mitochondrial membrane, as stated in L. Cercek & B. Cercek, "Involvement of Mitochondria in Changes of Fluorescein Excitation and Emission Polarization Spectra in Living Cells," *Biophys. J.*, 28, 403-412 (1979).

Immunologically the SCM-responding lymphocytes are T-cell mononuclear leukocytes Although not fully understood, it is believed that SCM-responding lymphocytes are involved in the recognition of antigens that are circulating in the blood stream. This recognition of antigens triggers the body's immune system. Accordingly, these cells become primed to recognize foreign substances, such as antigens, produced by the disease or condition affecting the body. Not all lymphocytes found in the bloodstream, however, are SCM-responding; only selected sub-populations of cells having specific and narrowly defined buoyant densities are SCM-responding.

In order to carry out the SCM test successfully, preferably the selected sub-population of SCM-responding lymphocytes must be isolated from other blood components, including all non-SCM-responding lymphocytes. In our prior work, as described in the 1977 *European Journal of Cancer* article, we isolated SCM-responding lymphocytes on Ficoll ™ -Triosil ™ gradients after removal of the phagocytic cells from the blood sample by treatment with iron powder or carbonyl-iron powder. The SCM-responding lymphocytes isolated were those that floated on top of a Ficoll-Triosil gradient with a density of 1.081 $g/cm^3$ and an osmolality of 0.320 Osm/kg, while non-responding cells banded inside the gradient. The density figure of 1.081 $g/cm^3$ refers to the density of the gradient solution itself; the actual buoyant density of the SCM-responding cells themselves was not determined, but must be somewhat less than 1.081 $g/cm^3$. The SCM-responding cells were collected from the gradient with a Pasteur pipette, taking great care to avoid the collection of blood components separated above the narrow band of SCM-responding lymphocytes or cells that separated in the density gradient solution below the narrow band. This procedure requires considerable practice and manual dexterity to carry out properly. Additionally, the conditions for isolation and separation of the SCM-responding lymphocytes, such as the temperature of the blood sample and the density gradient solution, and the density, osmolality, and pH of the solution must be rigorously controlled. For example, the temperature should be controlled to $\pm 0.2°$ C. Failure to control any of these isolation and separation conditions can result either in loss of some of the desired SCM-responding cells or the isolation of some of the non-responding cells along with the desired SCM-responding cells, as stated in L. Cercek & B. Cercek, "Effect of Osmolality and Density of Gradients on the isolation of SCM-Responding Lymphocytes," *Brit. J. Cancer* 38, 163-165 (1978). Such errors can result in loss of sensitivity of the SCM test. Indeed, a number of other laboratories attempting to corroborate our work have failed to obtain reliable and reproducible results because of poor or unskilled technique in the separation of the SCM-responding lymphocytes.

This need for precise separation of the SCM-responding lymphocytes became even more important when it was realized that there exists more than one subpopulation of SCM-responding cells, and that these subpopulations yield markedly different responses in the SCM test. The existence of such subpopulations was reported in the 1978 *Lancet* article by Pritchard et al., in the 1982 *European Journal of Cancer Clinical Oncology* article by Pritchard et al., and in J. M. Rolland, R. C. Nairn, A. P. Nind, and E. Pihl, "Significance of Lymphocyte Fluorescence Polarization Changes After Phytohaemagglutinin Stimulation in Cancer and Non-cancer Conditions," *J. National Cancer Institute* 72, 267-273 (1984). These studies revealed that besides the subset of SCM-responding cells that had been isolated in previous SCM studies, there exists an additional subset of SCM-responding cells with a buoyant density different from that of the first set. Unlike the SCM-responding cells previously studied, this additional subset of cells only responded to PHA, and did so only when isolated from cancer patients. It did not respond to any cancer-associated antigens such as CaBP, whether or not isolated from patients with malignancies, and failed to respond to PHA when isolated from patients without cancer. In summary, the response of this subset of cells to PHA is exactly the opposite of that of the first subset. Clearly, it is necessary to separate these two subsets of cells in performing the SCM assay. Otherwise, the results are impossible to interpret, especially when PHA is used to stimulate the SCM-responding cells.

The techniques used by Pritchard et al. and Rolland et al. to separate the two types of SCM-responding cells from each other and from other blood components were slight modifications of the technique described by us in our 1977 *European Journal of Cancer* article. In this technique, the two fractions of cells are isolated in rather ill-defined bands or zones near the interface between the blood plasma and the Ficoll-Triosil density gradient. In the use of such a technique, it has proven difficult to avoid cross-contamination of the cell fractions with each other and with SCM non-responding lymphocytes. Such cross-contamination is apparent, for example, in the results shown in Table 1 of the 1982 *European Journal of Cancer Clinical Oncology* article by Pritchard et al., where many patients show responses to PHA in both fractions of SCM-responding cells. Since only one fraction or the other of the SCM-responding cells actually responds to PHA, depending on whether or not the cells are isolated from patients with cancer, such a dual response clearly indicates the presence of cross-contamination.

An additional disadvantage of the prior methods of lymphocyte isolation has been the use of iron powder or carbonyl-iron powder in an initial step of removing the phagocytic cells from the blood sample. The use of such materials can cause toxic effects to the lymphocytes or their hemolysis. These deleterious effects, presumably caused by impurities in some batches of the iron powder or carbonyl-iron powder, occur sporadically, but are difficult to control when they do occur.

Accordingly there is a need for a method of isolating SCM-responding lymphocytes that can be carried out rapidly by workers with limited training, that does not require special dexterity, and that can reliably separate both subpopulations of SCM-responding cells without cross-contamination or contamination of either of the sub-populations with SCM-non-responding cells Preferably such a technique can also dispense with the use of carbonyl-iron powder or iron powder in the initial step of the procedure.

SUMMARY

The present invention discloses improved methods for isolating either the lower buoyant density F2 subpopulation, the higher buoyant density F4 subpopulation, or both subpopulations of SCM-responding lymphocytes from a blood sample. These methods avoid cross-contamination of the SCM-responding lymphocyte subpopulations or contamination of the desired lymphocytes with non-responding lymphocytes or other blood components.

The methods can use either the total population of peripheral blood lymphocytes or the entire sample of blood depleted of phagocytic cells as the starting material for the centrifugation step. Using the total population of peripheral blood lymphocytes as starting material avoids the use of carbonyl-iron powder or iron powder and is preferred.

When the F2 subpopulation of lymphocytes is isolated starting with the total population of peripheral blood lymphocytes, the method comprises the steps of:

(1) layering a first solution with an osmolality of between about 0.270 Osm/kg and about 0.330 Osm/kg at 20° C. and a density ($\rho_1$) determined by the equation $\rho_1 = 1.0572 + 0.063$ (X $-$ 0.290), Where X equals the osmolality of the first solution in Osm/kg, on top of a second solution with the same osmolality as the first solution and a density $\rho_2$ determined by the equation $\rho_2 = 1.0652 + 0.063$ (X $-$ 0.290). the volumes of the first and second solutions being sufficient to separate the F2 lymphocytes from other peripheral blood lymphocytes;

(2) layering a volume of peripheral blood lymphocytes of about one-half the total volume of the first and second solutions on top of the layered first and second solutions;

(3) centrifuging the mixture of peripheral blood lymphocytes and layered first and second solutions such that the F2 lymphocyte subpopulation is concentrated in a visible band between the layered first and second solution; and (4) collecting the visible band to obtain the F2 lymphocyte subpopulation, the collected lymphocytes being substantially free of lymphocytes having buoyant densities greater than 1.0670 g/cm³ or less than 1.0590 g/cm³, the buoyant densities being measured at 20° C. in a solution having an osmolality of about 0.315 Osm/kg.

The same method is used for isolation of the F4 lymphocyte subpopulation except that the density of the first solution is determined by the equation $\rho_1 = 1.0672 + 0.063$ (X$-$0.290), and the density of the second solution is determined by the equation $\rho_2 = 1.0712 + 0.063$ (X$-$0.290). When both the F2 and F4 subpopulations of SCM-responding lymphocytes are isolated simultaneously from the same gradient starting with the total population of peripheral blood lymphocytes, the method comprises the steps of:

(1) layering a first, second, third, and fourth solution with the same osmolality on top of each other to form a four-density solution stack:

(a) the first solution having an osmolality of between about 0.270 Osm/kg and about 0.330 Osm/kg at 20° C. and a density ($\rho_1$) determined by the equation $\rho_1 = 1.0712 + 0.063$ (X$-$0 290), where X equals the osmolality of the first solution in Osm/kg;

(b) the second solution having a density ($\rho_2$) determined by the equation $\rho_2 = 1.0672 + 0.063$ (X$-$0.290); p (c) the third solution having a density ($\rho_3$) determined by the equation $\rho_3 = 1.0652 + 0.063$ (X$-$0.290); and (d) the fourth solution having a density ($\rho_4$) determined by the equation $\rho_4 = 1.0572 + 0.063$ (X$-$0. 290); the first solution being positioned on the bottom of the solution stack, the volumes of the four solutions being sufficient to separate the F2 and F4 lymphocytes from each other and from other peripheral blood lymphocytes;

(2) layering a volume of peripheral blood lymphocytes of about one-half the total volume of the four-density solution stack on top of the solution stack;

(3) centrifuging the mixture of peripheral blood lymphocytes and the four-density solution stack such that the F2 lymphocyte subpopulation is concentrated in a visible band between the third and fourth solutions of the solution stack and the F4 lymphocyte subpopulation is concentrated in a visible band between the first and second solutions of the solution stack;

(4) collecting the visible band between the third and fourth solutions to obtain the F2 lymphocyte subpopulation, the collected lymphocytes being substantially free of lymphocytes having buoyant densities greater than 1.0670 g/cm, or less than 1.0590 g/cm³, the buoyant densities being measured at 20° C. in a solution having an osmolality of about 0.315 Osm/kg; and (5) collecting the visible band between the first and second solutions to obtain the F4 lymphocyte subpopulation, the collected lymphocytes being substantially free of lymphocytes having buoyant densities greater than 1.0730 g/cm³ or less than 1.0690 g/cm³, the buoyant densities being measured at 20° C. in a solution having an osmolality of about 0.315 Osm/kg.

In these methods, the solutions typically have an osmolality of 0.320 Osm/kg. At this osmolality, when only F2 lymphocytes are isolated, the first solution has a density of 1.0590 g/cm³ and the second solution has a density of 1.0670 g/cm³. When only F4 lymphocytes are isolated the first solution has a density of 1.0690 g/cm³ and the second solution has a density of 1.0730 g/cm³. When both F2 and F4 lymphocytes are isolated from the same gradient, the four solutions making up the solution stack have densities, respectively, of 1.0730 g/cm³, 1.0690 g/cm,, 1.0670 g/cm³, and 1.0590 g/cm³. In these methods, the two or four solutions can be solutions of polyvinylpyrrolidone-covered colloidal silica.

Any of these basic methods can further comprise the preliminary step of isolating the total population of peripheral blood lymphocytes from a heparinized blood sample by density gradient centrifugation in a medium capable of separating the peripheral blood lymphocytes from other blood components. This preliminary step can comprise the substeps of:

(1) layering heparinized blood on top of a solution of density 1.077 g/cm³ containing a non-ionic synthetic polymer of sucrose with a molecular weight of about 400,000 and sodium diatrizoate, the volume of the solution of density 1 077 g/cm³ being at least as great as the volume of heparinized blood, both solutions being equilibrated to room temperature;

(2) centrifuging the layered solutions at room temperature at sufficient effective gravitational force and for sufficient time so that the lymphocytes are banded at the interface between the solution of density 1.077 g/cm³ and the heparinized blood; and (3) collecting the lymphocytes from the interface.

Any of these isolation methods can be combined with the SCM test, resulting in a method for testing a blood sample for the presence of a condition or a disease based upon the response of the separated lymphocytes to contact with a challenging agent. As the response to particular challenging agents of the F2 subpopulation of SCM-responding lymphocytes differs from the response of the F4 subpopulation, the challenging agent varies with the subpopulation of SCM-responding lymphocytes isolated.

When both the F2 and F4 subpopulations of SCM-responding lymphocytes are isolated, the method can comprise the steps of:

(1) heparinizing the blood sample;

(2) isolating substantially all the peripheral blood lymphocytes from the heparinized blood sample;

(3) isolating separately both the F2 and F4 subpopulations of lymphocytes from the total population of peripheral blood lymphocytes by the four-density solution stack method described above;

(4) washing the isolated subpopulations of lymphocytes twice with saline and once with Dulbecco's complete phosphate buffered saline (PBS);

(5) contacting a first aliquot of the washed F2 lymphocyte subpopulation with a substance associated with the condition or disease being tested for; and (6) contacting the washed F4 lymphocyte subpopulation with a mitogen capable of stimulating T-cell lymphocytes.

When only the F2 subpopulation of lymphocytes is isolated, the method can comprise the steps of:

(1) heparinizing the blood sample;

(2) isolating substantially all the peripheral blood lymphocytes from the heparinized blood sample;

(3) isolating the F2 subpopulation of lymphocytes from the total population of peripheral blood lymphocytes as described above;

(4) washing the isolated F2 subpopulation of lymphocytes twice with saline and once with Dulbecco's complete phosphate buffered saline (PBS); and (5) contacting a first aliquot of the washed F2 lymphocyte subpopulation with a substance associated with the condition or disease being tested for.

When only the F4 subpopulation of lymphocytes is isolated and used in the SCM test the condition or disease tested for is necessarily cancer, because this lymphocyte subpopulation only shows a response in the SCM test to mitogens capable of stimulating T-cell lymphocytes and only when isolated from donors afflicted with cancer. This procedure can comprise the steps of:

(1) heparinizing the blood sample:

(2) isolating substantially all the peripheral blood lymphocytes from the heparinized blood sample;

(3) isolating the F4 subpopulation of lymphocytes from the total population of peripheral blood lymphocytes as described above;

(4) washing the isolated F4 subpopulation of lymphocytes twice with saline and once with Dulbecco's complete phosphate buffered saline (PBS); and (5) contacting the washed F4 lymphocyte subpopulation with the mitogen.

The challenging agent used to challenge the F2 lymphocyte fraction can be a cancer associated substance. It can alternatively be selected from viral and bacterial associated antigens or produced by the onset of allograft rejection crisis. The challenging agent can also be tissue extract, in which case the contacting step comprises determining compatibility for organ transplantation between a body from which the blood sample was obtained and a body from which the tissue extract was obtained.

The mitogen capable of stimulating T-cell lymphocytes is typically reagent grade phytohaemagglutinin PHA). When the F2 subpopulation of lymphocytes is isolated, a second aliquot of the washed F2 lymphocyte subpopulation can also be contacted with the mitogen, and the change in the SCM response of the mitogen-contacted second aliquot as a result of the contact monitored.

Similar gradient procedures can be used to isolate the F2 and/or F4 subpopulations of SCM-responding lymphocytes directly from a heparinized blood sample.

The method for isolating the F2 subpopulation directly from a heparinized blood sample comprises the steps of:

(1) removing the phagocytic cells from the heparinized blood sample by incubation of the blood sample with a powdered magnetic substance selected from the group consisting of carbonyl-iron powder and iron powder, followed by separation of the phagocytic cells from the remainder of the blood sample by application of magnetic force; and (2) isolating the F2 subpopulation of lymphocytes from the blood sample depleted of phagocytic cells by the steps of:

(a) layering a first solution with an osmolality of between about 0.270 Osm/kg and about 0.330 Osm/kg at 20° C. and a density ($\rho_1$) determined by the equation $\rho_1 = 1.0572 + 0.063 (X - 0.290)$, where X equals the osmolality of the first solution in Osm/kg, on top of a second solution with the same osmolality as the first solution and a density ($\rho_2$) determined by the equation $\rho_2 = 1.0652 + 0.063 (X - 0.290)$, the volumes of the first and second solutions being sufficient to separate the F2 lymphocytes from other lymphocytes present in the blood sample depleted of phagocytic cells;

(b) layering a volume of the blood sample depleted of phagocytic cells of about one-half the total volume of the first and second solutions on top of the layered first and second solutions;

(c) centrifuging the mixture of the blood sample depleted of phagocytic cells and layered first and second solutions such that the F2 lymphocyte subpopulation is concentrated in a visible band between the layered first and second solutions; and (d) collecting the visible band to obtain the F2 lymphocyte subpopulation substantially free of lymphocytes outside the density limits of the fraction;

A similar procedure can be used for isolating the F4 lymphocyte subpopulation, with the densities of the first and second solutions being determined as previously described When both the F2 and F4 subpopulation of lymphocytes are isolated from a single gradient, the four-density solution stack previously described is used.

More generally, the present invention includes methods for testing a blood sample for the presence of a condition or a disease based upon the response of the lymphocytes separated from the blood sample to contact with a substance associated with the condition or disease being tested for. The lymphocyte response is indicated by changes in the SCM of the lymphocytes as a result of contact between the lymphocytes and the substance.

When both the F2 and F4 subpopulations of lymphocytes are isolated from the same blood sample, the method comprises the steps of:

(1) isolating from the blood sample two discrete fractions of lymphocytes, an F2 fraction containing lymphocytes having buoyant densities of from about 1.0590 g/cm$^3$ to about 1.0670 g/cm$^3$ and an F4 fraction having buoyant densities of from about 1.0690 g/cm$^3$ to about 1.0730 g/cm$^3$, each fraction being substantially free of lymphocytes having buoyant densities other than those defining the fraction, the buoyant densities being measured at 20° C. in a solution having an osmolality of about 0.315 Osm/kg;

(2) washing the isolated fractions of lymphocytes twice with saline and once with Dulbecco's complete PBS;

(3) contacting the F2 fraction with the substance; and (4) contacting the isolated F4 fraction with a mitogen capable of stimulating T-cell lymphocytes, the mitogen typically being reagent grade PHA.

When only the F2 subpopulation of lymphocytes is isolated, the comparable method comprises the steps of;

(1) isolating from the blood sample a discrete F2 fraction of lymphocytes containing lymphocytes having buoyant densities of from about 1.0590 g/cm$^3$ to about 1.0670 g/cm$^3$, the fraction being substantially free of lymphocytes having buoyant densities other than those defining the fraction;

(2) washing the isolated F2 fraction of lymphocytes twice with saline and once with Dulbecco's complete PBS; and (3) contacting the isolated F2 fraction with the substance.

As stated previously, the condition or disease associated substance can be a cancer associated substance, or can be selected from viral and bacterial associated antigens. The substance can also be tissue extract or a substance produced by the onset of allograft rejection crisis.

When either the F2 fraction alone or both the F2 and F4 fractions of lymphocytes are isolated, the method can also comprise the additional steps of also contacting the isolated washed F2 fraction of cells resuspended in Dulbecco's complete PBS with the mitogen capable of stimulating T-cell lymphocytes and monitoring the response of the mitogen contacted F2 fraction to the mitogen by observing SCM changes as a result of the contact.

In the method, the step of isolating the two discrete fractions of lymphocytes can comprise the steps of:

(a) centrifuging a solution at a sufficient effective gravitational force to preform a multi-density gradient having a minimum density of no greater than about 1.050 g/cm$^3$ and a maximum density of no less than about 1.070 g/cm$^3$ when the F2 lymphocyte subpopulation is isolated, or a maximum density of no less than about 1.080 g/cm$^3$. When both the F2 and F4 lymphocyte subpopulations are isolated; and (b) centrifuging the blood sample in the preformed gradient.

The step of isolating the discrete lymphocyte fractions can also comprise centrifuging the blood sample in a multi-density gradient solution comprising a mixture of at least two fluids of equal osmolality, the maximum density of the gradient being the density of the most dense fluid and the minimum density of the gradient being the density of the least dense fluid.

The present invention also includes methods for classifying and separating from a blood sample lymphocytes capable of responding to stimulation by: (a) a substance associated with a disease or condition or (b) a mitogen capable of stimulating T-cell lymphocytes. The response is exhibited by measurable changes in the SCM of the lymphocytes upon contact between the lymphocytes and the substance or the mitogen.

When both the F2 and F4 subpopulations of lymphocytes are to be isolated, the method comprises the steps of:

(1) forming a multi-density gradient solution having a minimum density of no greater than about 1.050 g/cm$^3$ at 20° C. and a maximum density of no less than about 1.080 g/cm$^3$ at 20° C.

(2) combining the blood sample with the multi-density gradient solution;

(3) centrifuging the blood sample in the multi-density gradient solution at a controlled temperature and at sufficient effective gravitational force to cause components of the blood sample to separate and be distributed and retained in the multi-density gradient solution according to the buoyant densities of the blood components;

(4) separating aliquots of the multi-density gradient solution in discrete fractions, the aliquots containing the portions of the multi-density gradient solution having densities respectively of from about 1.0590 g/cm$^3$ to about 1.0670 g/cm$^3$ and from about 1.0690 g/cm$^3$ to about 1.0730 g/cm$^3$ ; and (5) separately washing the two aliquots to obtain two suspensions of lymphocytes, the lymphocytes in at least one of the suspensions being capable of responding to stimulation by either the condition or disease associated substance or the mitogen.

Each of the suspensions is substantially free of lymphocytes having buoyant densities other than those defining the collected aliquots.

When only the F2 subpopulation is to be isolated, a similar procedures is used, except that the multi-density gradient solution has a maximum density of no less than about 1.070 g/cm³ at 20° C., and only one aliquot of the gradient is collected after centrifugation. This aliquot contains that portion of the multi-density gradient having densities of from about 1.0590 g/cm³ to about 1.0670 g/cm³ at 20° C.

Typically, the multi-density gradient comprises a continuous density gradient, and has an osmolality of about 0.315 to about 0.320 Osm/kg. The multi-density gradient solution can comprise an aqueous solution of colloidal silica diluted with saline solution; the colloidal silica is typically coated with an inert material. The multi-density gradient can alternatively comprise a mixture of two fluids of equal osmolality.

The blood sample is typically centrifuged at about 550 g at 20° C. in the multi-density gradient solution.

The F4 lymphocyte subpopulation alone can be isolated by analogous methods in a method for testing a blood sample from a donor for the presence of cancer in the donor, or in a method for classifying and separating from a blood sample lymphocytes capable of responding to stimulation by a mitogen capable of stimulating T-cell lymphocytes. Only cancer can be tested for using the F4 subpopulation of SCM-responding lymphocytes.

The gradient for the isolation of the F4 lymphocyte subpopulation alone has a minimum density of no greater than about 1.060 g/cm³ and a maximum density of no less than about 1 080 g/cm³. The fractions or aliquots collected have buoyant densities of from about 1.0690 g/cm³ to about 1.0730 g/cm³ at 20° C.

DRAWINGS

Figure 2:
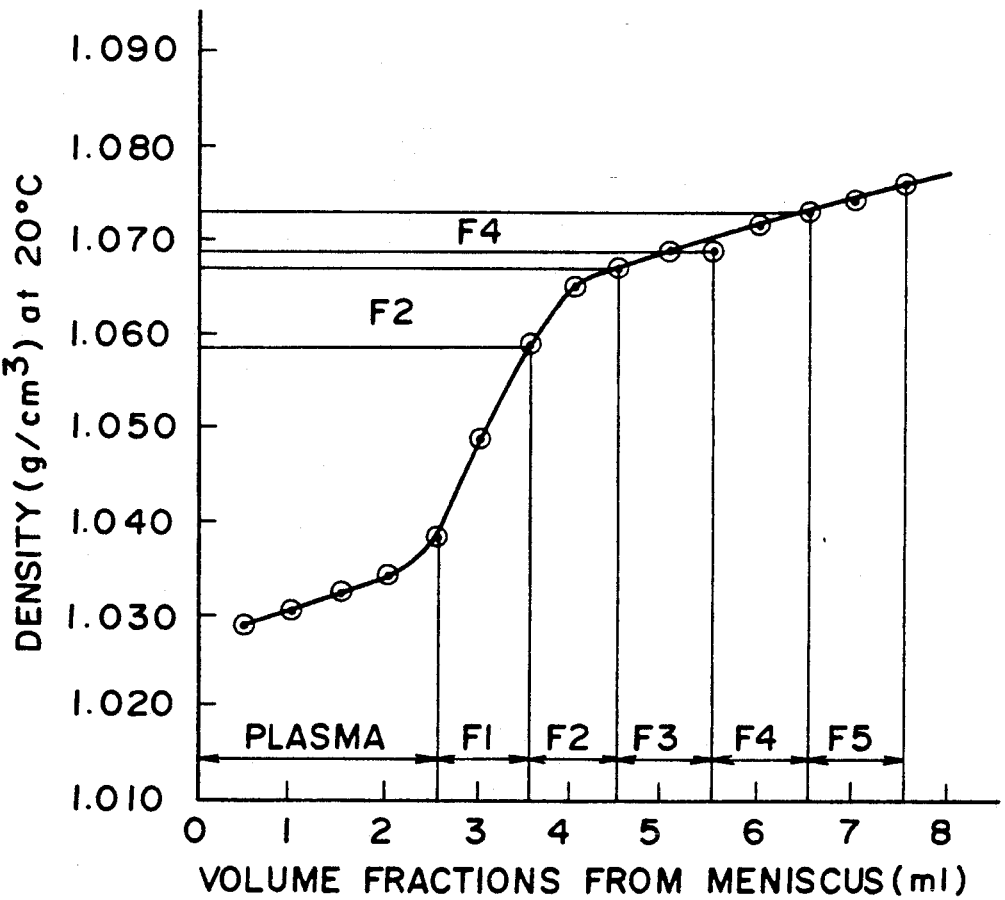

These and other features, aspects, and advantages of the present invention will become better understood with reference to the following description, appended claims, and accompanying drawings where:

FIG. 1 is a plot of density versus volume measured from the meniscus of a continuous preformed density gradient solution used in the invention; and FIG. 2 is a plot of density versus the volume fractions taken from such a gradient, showing the density ranges in which the SCM-responding cells are located.

DESCRIPTION

The procedures of the present invention can isolate either or both subsets of SCM-responding lymphocytes from a single blood sample as desired. The subset of SCM-responding lymphocytes previously studied by us, and which responds with a decrease in SCM when exposed to PHA when isolated from donors free of cancer but responds with a decrease in SCM when exposed to cancer-associated antigens when isolated from donors with cancer, is designated the F2 lymphocyte fraction. The other subset of SCM-responding lymphocytes, which responds only to PHA and only when isolated from patients with cancer, is designated the F4 lymphocyte fraction. The F2 lymphocyte fraction has buoyant densities of from 1.0590 g/cm³ to 1.0670 g/cm³ as measured at 20° C. at an osmolality of 0.315 Osm/kg. The F4 lymphocyte fraction has buoyant densities of from 1.0690 g/cm³ to 1.0730 g/cm³ under the same conditions. Lymphocytes falling outside these densities are not SCM-responding in the test procedure described herein and their presence should be avoided as diluting the effect of the SCM-responding cells. This dilution can result in a reduction in test sensitivity.

The term "solution" as used herein refers to both true solutions and to suspensions comprising partially or wholly colloidal material such as polyvinylpyrrolidone-covered colloidal silica that behave equivalently to true solutions under the centrifugation procedure of the present invention. The term "buoyant density" as used herein designates the density of that position of the multi-density gradient solution at which a particular blood component is essentially at zero gravity At its buoyant density, the component neither exhibits buoyancy nor sinks in the gradient. Blood components, including different lymphocyte fractions, have different buoyant densities thus rendering possible their separation in the multi-density gradient solution.

As already mentioned, the buoyant densities referred to herein are taken at the standard conditions of 20° C. and 0.315 Osm/kg. In certain cases it can be inconvenient to operate at standard conditions. In such cases the actual buoyant densities of the blood components that are separated at non-standard conditions are calculated back to standard conditions according to the following equations:

$$D_x = D_{0.315} + 0.063(x - 0.315); \text{ and}$$

$$D_{t°} = D_{20° C.} + 2.8 \times 10^{-4}(20° C. - T°C.),$$

where $D_x$ and $D_t°$ are buoyant densities at the osmolality of $x$ Osm/kg and $T°C.$, respectively.

A. Isolation of SCM-Responding Lymphocytes After Separation of Phagocytic Cells from the Blood Sample For some purposes, it can be desirable to perform the isolation of SCM-responding lymphocytes after the separation of the phagocytic cells from the blood sample by treatment with iron powder or carbonyl-iron powder.

1. Separation of the Phagocytic Cells

The phagocytic cells are removed from the blood sample by incubation of the blood sample with a powdered magnetic substance followed by separation of the phagocytic cells from the remainder of the blood sample by application of magnetic force. The powdered magnetic substance is typically iron powder or carbonyl-iron iron powder. This procedure is described in L. Cercek, B. Cercek, and C. I. V. Franklin, "Biophysical Differentiation Between Lymphocytes from Healthy Donors, Patients with Malignant Diseases and Other Disorders," *British J. Cancer* 29, 345-352 (1974) and in our *European Journal of Cancer* article, both of which are incorporated herein by this reference. Other methods of removing phagocytic cells can also be used.

Generally, 0.1 g of the iron powder or carbonyl-iron powder is added to 10 ml of a heparinized blood sample and the blood sample containing the powder is first rotated, then placed on a magnet to effect separation of phagocytic cells from the remainder of the blood sample. The phagocytic cells, having ingested the magnetic particles, are pulled to the bottom of the sample, and the supernatant, consisting of the remainder of the blood sample depleted of phagocytic cells, is removed. Further details of this procedure are given in Example 1.

2. Isolation of the SCM-Responding Lymphocytes a. The Gradient

The separation method of the invention employs a multi-density gradient solution to isolate the SCM-responding lymphocytes within narrowly defined density intervals as required by the SCM test procedure outlined above. The range of densities in the gradient brackets the density intervals within which either the F2 SCM-responding lymphocytes, or the F4 SCM-responding lymphocytes, or both, occur, depending upon which cells are to be collected. If only the F2 cells are to be collected, the minimum density of the gradient is no greater than 1.050 g/cm$^3$ and the maximum density of the gradient is no less than 1.070 g/cm$^3$. If only the F4 cells are to be collected, the corresponding minimum and maximum densities are 1.060 g/cm$^3$ and 1.080 g/cm$^3$. If both the F2 and F4 cells are to be collected from a single gradient, the corresponding minimum and maximum densities are 1.050 g/cm$^3$ and 1.080 g/cm$^3$. The interval between the maximum and minimum densities optimally is not significantly greater than 0.020 g/cm$^3$ if only one fraction of SCM-responding cells is to be collected or 0.030 g/cm$^3$ if both cell fractions are to be collected. Otherwise, loss of resolution can result.

Several methods can be used to produce a multi-density gradient solution for use in the present invention. The multi-density gradient solution can be preformed by centrifugation before layering the cells on the gradient. The preformed gradient can be prepared by centrifuging a solution of an inert colloidal material such as polyvinylpyrrolidone-coated silica at sufficient effective gravitational force to form a solution having a density profile that continuously increases between the minimum and maximum densities of the gradient. For a preformed density gradient solution, the density profile is dependent on the effective gravitational force used to establish it, the temperature, and the osmolality of the solution. In general, the greater the effective gravitational force used to establish the gradient, the steeper the density profile of the gradient. We have found that the desired continuous density profile can be obtained by centrifuging the solution using a fixed 29° angle rotor at the standard conditions of temperature and osmolality at 26,000 $g_{AV}$. With a 34° angle rotor the same density profile is obtained by centrifuging at 11,400 $g_{AV}$.

Alternatively, a step gradient can be formed by layering fluids bracketing the buoyant densities of the desired F2 and/or F4 lymphocytes. If it is desired to isolate the F2 lymphocytes, a given volume of a solution of density 1.0670 g/cm$^3$ and osmolality 0.320 Osm/kg at 20° C. is first placed in a centrifuge tube. On top of this solution, an equal volume of a solution of density 1.0590 g/cm$^3$ and osmolality of 0.320 Osm/kg at 20° C. is layered slowly. These solutions are typically prepared from polyvinylpyrrolidone-covered silica media such as Percoll ™, distributed by Pharmacia, but other density gradient media nontoxic to lymphocytes, such as Histopaque ™, distributed by Sigma Diagnostics, and consisting of a nonionic synthetic polymer of sucrose in an aqueous solution of sodium diatrizoate, can also be used. If only the F4 fraction of lymphocytes is isolated, the lower solution has a density of 1.0730 g/cm$^3$ and the upper solution has a density of 1.0690 g/cm$^3$. If both the F2 and F4 fractions of lymphocytes are isolated, a four-density solution stack is prepared, with solutions of densities of 1.0730 g/cm$^3$, 1.0690 g/cm$^3$, 1.0670 g/cm$^3$, and 1.0590 g/cm$^3$ being successively layered on top of each other. The use of such a two-component or four-component step gradient is preferred when SCM-responding cells are isolated from the total lymphocyte population, as described below.

b. Centrifugation of Blood Samples and Collection of Lymphocyte Fractions

To separate the lymphocyte fractions, an aliquot of the blood sample depleted of phagocytic cells is layered on the multi-density gradient prepared as described above. The combination is then centrifuged at sufficient effective gravitational force to separate the blood components in the multi-density gradient solution according to their respective buoyant densities This centrifugation is generally performed at much lower effective gravitational force than the effective gravitational force used to preform the gradient. As described in more detail in the Examples below, the effective gravitational force used to separate the lymphocytes is typically between about 550 $g_{AV}$ and about 1100 $g_{AV}$.

After centrifugation, consecutive equivolume aliquots of the multi-density gradient are withdrawn by aspiration or titration and the density of each aliquot determined. The aliquots of density corresponding to the desired F2 and/or F4 lymphocyte fractions are saved, and the desired aliquots are then washed for use in the SCM test as indicated below in the Examples.

When a step gradient with solutions of densities of 1.0670 g/cm$^3$ and 1.0590 g/cm$^3$ (for F2 lymphocytes) or 1.0730 g/cm$^3$ and 1.0690 g/cm$^3$ (for F4 lymphocytes) is used, or when a four-density solution stack is used for the isolation of both F2 and F4 lymphocytes, the desired F2 and/or F4 subpopulations isolate as visible bands, about 2 mm in height, at the interface between two solutions of differing density in the step gradient or solution stack The F2 lymphocytes isolate between the solution of density 1.0590 g/cm$^3$ and the solution of density 1.0670 g/cm$^3$, while the F4 lymphocytes isolate between the solution of density 1.0690 g/cm$^3$ and the solution of density 1.0730 g/cm$^3$. These visible bands can be collected directly from the gradient.

B Isolation of SCM-Responding Lymphocytes from Total Lymphocyte Population

As an alternative to the isolation of the F2 or F4 fractions of SCM-responding lymphocytes from the entire blood sample after depletion of phagocytic cells, the fractions of SCM-responding lymphocytes can be isolated after the prior isolation of the entire population of peripheral blood lymphocytes. This not only simplifies the procedure, but also prevents possible toxic effects or hemolysis caused by impurities in some batches of the carbonyl-iron or iron powder. This variation of the procedure also eliminates slight changes in the density gradient positions of the F2 and F4 fractions of SCM-responding lymphocytes caused by differences in the hematocrit of the blood donors The isolation of the peripheral blood lymphocytes can be performed by a number of methods, but is preferably performed by layering a heparinized blood sample on a solution with density 1.077 g/cm$^3$ containing a nonionic synthetic polymer of sucrose with a molecular weight of about 400,000 and sodium diatrizoate, and then centrifuging the mixture. A suitable solution is Histopaque-1077 $_{TM}$, distributed by Sigma Diagnostics. Typically, the centrifugation is performed at 550 $g_{AV}$ for 30 minutes at room temperature. All lymphocytes banded at the interface between the density solution and the blood plasma are collected into a single centrifuge tube. The cells are then washed and resuspended in 0.9% saline for isolation of the F2 and/or F4 fraction of SCM-responding lymphocytes. Preferably, the subsequent isolation of the SCM-responding lymphocytes is carried out by the step gradient or four-density solution stack methods, as described above under "Centrifugation of Blood Samples and Collection of Lymphocyte Fractions." These methods yield the lymphocyte fractions of interest in visible bands Collection of the SCM-responding lymphocyte fractions can be carried out manually or with an automated cell collector.

As mentioned, other methods well known in the art can be used to isolate the total lymphocyte population, such as the precipitation of erythrocytes with dextran such as isotonic T500 dextran.

EXAMPLES

EXAMPLE 1

Preparation of Preformed Continuous Density Gradient

A preformed continuous density gradient was prepared by mixing 56 parts by volume of a 9% (w/v) solution of polyvinylpyrrolidone-covered colloidal silica (Percoll $_{TM}$) marketed by Pharmacia AB) in sterile water with 44 parts per volume of a saline solution comprising 0.34M NaCl and 0.2 g/l $KH_2PO_4$ in sterile preservative-free water. The density of the solution prior to centrifugation was checked with a Paar Digital Density Meter, Model DMA 55, and was found to average about 1.077 g/cm$^3$ at 20° C. The solution was sterilized by filtration through an 0.22 micron Millipore $_{TM}$ filter. The solution was prepared in 1000-ml quantities and could be stored for up to 2 months in a dark bottle at 4° C.

Fifteen-milliliter aliquots of this solution were transferred to glass centrifuge tubes with 16 mm O.D. and brought to a temperature of 20° C. The aliquots were centrifuged for 30 minutes at 26,000 $g_{AV}$ using a fixed 29° angle rotor to preform the gradient. The density profile of the solution after centrifugation was determined by measuring the density of each consecutive ml fraction at 20° C. using the Paar Digital Density Meter. A plot of the density of each of the consecutive fractions is shown in FIG. 1. As shown, there was a continuous increase in the density of the fractions, from the second volume fraction at a density of about 053 g/cm$^3$ to the twelfth volume fraction at a density of about 1.090 g/cm$^3$.

EXAMPLE 2

Separation of SCM-Responding Lymphocytes Using the Gradient of Example 1

Twenty-milliliter samples of peripheral blood were obtained from 30 healthy donors and 20 donors who had been positively diagnosed as having a malignancy. For the purposes of the example, the specific type of cancer is not critical.

The blood samples were collected in LH/10 lithium heparin-containing blood collection tubes distributed by Searle or in heparinized Vacutainer $_{TM}$ tubes. Heparinized blood samples can be stored at room temperature 18° C. to 20° C.) for up to 12 hours. Ten milliliters of each blood sample was transferred to a separate 20 ml glass vial containing 0.1 g carbonyl-iron powder (type SF distributed by GAF, Ltd., Great Britain). Equivalent results have been achieved using iron powder distributed by Koch-Light Laboratories, Ltd. and identified as 8365×99.5%. The vials were rotated at 30 revolutions per minute for 30 minutes at 37° C. and then placed on a magnet for 15–30 minutes to effect separation of the phagocytic cells along with the iron powder from the blood sample.

A four-to-five milliliter aliquot of each of the blood samples depleted of phagocytes was transferred to a centrifuge tube containing the continuous density gradient solution prepared in Example 1 and from which the top 4 ml of the density gradient solution had been removed. Both the density gradient solution and the blood aliquot had been equilibrated to a temperature of 20° C. before the transfer The transfer was accomplished by layering the blood on top of the density gradient solution The tubes were placed in a centrifuge that was thermostatically controlled to maintain a temperature of about 20° C. and gradually accelerated over 1 minute to 550 $g_{AV}$ and held at that speed for 30 minutes No brake was applied during deceleration Consecutive 0.5 ml aliquots were removed from the tubes and the density of each aliquot was determined at 20° C. with the Paar Digital Density Meter.

Examination of consecutive 0.5 ml aliquots removed from each of the centrifuge tubes after centrifugation showed that the first five aliquots removed, representing the top 2.5 ml of the gradient, contained essentially cell-free plasma. The next two aliquots, representing that portion of the gradient from 2.5 ml to 3.5 ml, contained approximately 98% lymphocytes. These two aliquots were combined and designated fraction 1 (F1). The blood components isolated in the next two aliquots, spanning that portion of the gradient from 3.5 ml to 4.5 ml, comprised nearly 100% lymphocytes. These two aliquots were combined as fraction 2 (F2). The third fraction (F3) was a combination of the next two aliquots of the gradient, spanning that portion of the gradient from 4.5 ml to 5.5 ml. This fraction contained about 99% lymphocytes. The fourth fraction (F4) was a combination of the next two aliquots of the gradient from 5.5 ml to 6.5 ml, and contained about 80% lymphocytes The last fraction collected, fraction 5 (F5), was a combination of the next two aliquots of the gradient from 6.5 ml to 7.5 ml, and contained about 75% lymphocytes The remaining aliquots of the gradient contained mainly erythrocytes and were discarded. The blood components other than lymphocytes in the fractions F1-F5 comprised mostly erythrocytes, although some granulocytes or platelets were also observed.

The density range of each of the fractions was taken as the minimum density of the first aliquot forming the fraction to the maximum density of the second aliquot forming the fraction. Table 1 is a summary of the density ranges and the percentage of lymphocytes in the blood components in fractions 1-5 as collected from the density gradient.

TABLE 1

DENSITY RANGES OF FRACTIONS TAKEN FROM GRADIENT OF EXAMPLE 2 AND PERCENTAGES OF LYMPHOCYTES IN FRACTIONS

| Fraction No. | Aliquot, ml$^a$ | Density, g/cm$^3$ | % Lymphocytes |
|---|---|---|---|
| 1 | 2.5–3.5 | 1.0385–1.0590 | 98.6 |
| 2 | 3.5–4.5 | 1.0590–1.0670 | 99.7 |
| 3 | 4.5–5.5 | 1.0670–1.0690 | 99.4 |
| 4 | 5.5–6.5 | 1.0690–1.0730 | 80.0 |
| 5 | 6.5–7.5 | 1.0730–1.0760 | 75.0 |

Densities were measured at 20° C. and at an osmolality of 0.315–0.320 Osm/kg.
$^a$Measurement of aliquots taken was from meniscus of gradient.

EXAMPLE 3

Isolation of Total Population of Peripheral Blood Lymphocytes

For this separation, 20 ml of heparinized blood treated with 300 I.V. of heparin/10 ml of blood) was layered in 5-ml aliquots on 5-ml aliquots of Histopaque 1077 $_{TM}$) distributed by Sigma Diagnostics) in 15-ml 16 mm O.D.) centrifuge tubes Both the blood and the Histopaque solution were equilibrated to room temperature before layering. The layered solutions were then centrifuged at 550 $g_{AV}$ for 30 minutes at room temperature All lymphocytes isolated at the interface between the density solution and the blood plasma were collected into a single centrifuge tube The collected cells were washed once with 0.9% saline, pelleted by centrifugation at 550 $g_{AV}$ for 5 to 10 minutes, and resuspended in 4 ml of 0.9% saline for the second isolation step, the isolation of the SCM-responding fraction of lymphocytes.

EXAMPLE 4

Isolation of F2 Fraction of SCM-Responding Lymphocytes from Total Population of Peripheral Blood Lymphocytes Two density solutions, prepared from Percoll$_{TM}$) (Pharmacia AB), were used for isolation of the F2 fraction of SCM-responding lymphocytes from the total population of peripheral blood lymphocytes (Example 3). The step gradient used was prepared as follows: First, four milliliters of a density solution with a density of 1.0670 g/cm$^3$ at 20° C. and an osmolality of 0.320 Osm/kg (Solution A) was dispensed into a 15-ml glass centrifuge tube with an O.D. of 16 mm. On top of this solution, four milliliters of a density solution with a density of 1.0590 g/cm$^3$ and osmolality of 0.320 Osm/kg (Solution B) was layered slowly to form a bilayer of density solutions. On top of this bilayer, four milliliters of the suspension of the total population of peripheral blood lymphocytes from Example 3 was layered. Both the bilayer and the suspension of lymphocytes were equilibrated to 20°±1° C.

The F2 sub-population of SCM-responding lymphocytes isolated as a visible band, about 2 mm in height, between the density solutions A and B, and the band was collected directly. After collection, the lymphocytes were washed twice with preservative-free 0.9% saline for injections, then once or twice with Dulbecco's complete phosphate buffered saline (PBS), and then resuspended in 1 to 2 ml of PBS.

EXAMPLE 5

Isolation of Both F2 and F4 Fractions of SCM-Responding Lymphocytes from Total Population of Peripheral Blood Lymphocytes The procedure of Example 4 was used, except that the lymphocyte suspension of Example 3 was layered on a four-density solution stack prepared by layering on top of each other 3 ml aliquot of Percoll solutions with the following densities at 20° C. and osmolalities of 0.320 Osm/kg: 1.0730 g/cm$^3$ (Solution D) ; 1.0690 g/cm$^3$ (Solution C); 1.0670 g/cm$^3$ (Solution B); and 1.0590 g/cm$^3$ (Solution A), with solution D on the bottom of the stack When this four density solution stack was used, the F2 sub-population of SCM-responding lymphocytes was isolated as a visible band at the interface between Solution A and B, while the F4 sub-population was isolated as a visible band at the interface between solutions C and D.

EXAMPLE 6

Determination of SCM Response to Cancer-Associated Antigen

Each fraction obtained in Example 2 was checked for the SCM response of the lymphocytes in the fraction in accordance with the SCM cancer screening procedure as described in the article by L. Cercek and B. Cercek, "Application of the Phenomenon of Changes in the Structuredness of Cytoplasmic Matrix (SCM) in the Diagnosis of Malignant Disorders: A Review," *Europ. J Cancer* 13, 903–915 (1977).

Each fraction was washed twice with 6–7 ml of an 0.9% solution of NaCl in sterile water followed by washing in Dulbecco's complete phosphate buffered saline (PBS) Between washes the cell suspensions were centrifuged at 500 $g_{AV}$ and the supernatant liquid was decanted. After washing, the cell suspension from each fraction was separately recombined with PBS and the volumes adjusted to form suspensions of about $5 \times 10^6$ cells/ml. The cell suspension of each fraction was divided into three portions: one portion to be used as a control, a second portion to be incubated with mitogen, and the third portion to be incubated with cancer-associated antigen.

In accordance with the procedure of the SCM test, stimulation of the lymphocytes was accomplished by incubating an 0.5 ml aliquot of each of the lymphocyte portions from each fraction with either 0.05 ml of the mitogen (PHA) or with 0.05 ml of the cancer-associated antigen for at least 30 minutes. The mitogen was reagent grade PHA obtained from Wellcome Ltd. or Gibco and was reconstituted and then diluted 1:5 to 1:10 with preservative-free sterile water for injections. The cancer-associated antigen was cancer basic protein (CaBP) obtained in accordance with previously disclosed techniques by extraction in PBS from a pool of cancer tissues obtained from various types of malignancies.

SCM responses were measured with a fluorescence spectrophotometer equipped with polarization accessories to measure vertically and horizontally polarized fluorescence emissions. The excitation monochromator was set at a wavelength of 470 nm and the emission monochromator at 510 nm. The fluorescence spectrophotometer used was a Perkin-Elmer MPF-4 instrument equipped with a thermostatically controlled cuvette holder, and the measurements were carried out at 27° C. A polarized filter for transmitting only vertically polarized light was mounted between the excitation monochromator and the sample. A second polarization filter was fitted with an automatic filter position changer for moving the filter between a first position for transmitting vertically polarized light and a second position for transmitting horizontally polarized light. The assembly of the filter and the position changer was mounted in the light path between the sample and the emission monochromator. The filters were Folacoat$_{TM}$ Type 105 UV sheet polarizers mounted between quartz discs.

Two-tenths of a milliliter of a control portion of the lymphocytes or a portion of the lymphocytes stimulated by PHA or CaBP was injected into a beaker containing 3 ml of an 0.6 μM solution of fluorescein diacetate in sterile PBS The FDA readily permeates the cell membrane and is converted into fluorescein molecules by enzymatic hydrolysis. A substantial portion of the fluorescein is retained by viable lymphocytes The measurement temperature of 27° C. was selected as a compromise, since the rate of FDA hydrolysis increases with temperature, but the rate of permeation of fluorescein from inside the cells also increases with temperature.

The reproducibility of the fluorescence polarization values obtained is also dependent on the osmolality and the pH of the FDA solution. The pH of the cell suspension was maintained at or slightly above 7.4, since the SCM response of lymphocytes decreases when the pH of the FDA solution is less than 7.4. The osmolality of the FDA solution was held to within ±1% of the isotonic value of 0.330 Osm/kg to ensure reproducibility between samples, as the measured polarization value of the cells increases with osmolality.

After the injection of the cell suspension into the FDA solution, the combination was immediately transferred to a quartz cuvette and placed in the thermostatically controlled cuvette holder. The intensities of the fluorescence parallel and perpendicular to the vertically polarized exciting light were measured by alternating the orientation of the polarization filter located between the sample and the emission monochromator and the measurements were recorded for about 6 minutes or until the intensity of the fluorescence perpendicular to the plane of the polarized exciting light reached about 80-90% of full scale deflection, whichever occurred first. Fluorescein leakage from the cells and background fluorescence were corrected for by gently filtering the cell suspension under controlled suction (less than 40 cm of Hg) and recording the emissions of the filtrate in the same manner as for the cell suspension. The fluorescence intensities emitted by the cells, $I_P$ and $I_N$, were obtained by subtracting the corresponding intensities of the filtrate from the total fluorescence intensities of the filtrate from the total fluorescence intensities extrapolated to the half time of the filtration internal. The polarization or P value of the cells in the sample was calculated from the relationship;

$$P=(I_P-GI_N)/(I_P+GI_N).$$

where $I_P$ and $I_N$ are polarized fluorescence emission intensities parallel and perpendicular respectively to the vertically polarized light source emitted by the cells of the sample and G is a correction factor for the unequal transmission of the parallel and perpendicular components of the polarized light through the optical system.

The value of G is determined by dividing the perpendicular fluorescence intensity emitted from a filtrate solution or from a $10^{-7}$M solution of fluorescein in PBS excited with horizontally polarized light at 470 nm by the parallel fluorescence intensity from the same solution under the same conditions. For the equipment used in this example, $G=0.42$.

For each of the five lymphocyte fractions, F1 to F5, whose isolation was described in Example 2, the mean P values for samples stimulated with PHA and cancer-associated antigen were determined as a percentage of the mean P value of stimulated control samples from each of the fractions as isolated from 30 healthy donors and from 20 donors who had been positively diagnosed as having a malignancy These results are summarized in Table 2 below Table 2 shows that the lymphocytes present in fractions 1, 3, and 5 of the continuous density gradient were SCM non-responding For the cells of fractions 1 and 3, there was essentially no response to simulation by either PHA or the cancer-associated antigen For the cells of fraction 5, the lymphocytes from healthy donors exhibited no response to the mitogen, indicating that the cells were also SCM non-responding. This was confirmed by the failure of these cells to exhibit a fluorescence polarization peak at 510 nm, in contrast to the cells of fractions 2 and 4. The cells of fraction 2 (F2 cells) exhibited classic SCM responses to stimulation by PHA and cancer-associated antigen. For example, F2 lymphocytes from healthy donors had a marked percentage decrease in polarization value when stimulated by PHA as compared to unstimulated control cells from the same fraction This indicated an SCM response by the lymphocytes to PHA These same lymphocytes had essentially no SCM response to the cancer-associated antigen. Similarly, F2 lymphocytes from donors afflicted with cancer had no SCM response to PHA but had a definite SCM response to the cancer-associated antigen. This shows that F2 lymphocytes, which have a buoyant density of 1.0590 g/cm$^3$ to 1.0670 g/cm$^3$ at 20° C. and an osmolality of 0.315 Osm/kg, are suitable for use in the SCM test for the detection of cancer.

The F4 lymphocytes, which have a buoyant density of 1.0690 g/cm$^3$–1.0730 g/cm$^3$ at 20° C. and an osmolality of 0.315 Osm/kg, also demonstrated an SCM response to PHA that would indicate usefulness in the SCM cancer test. However, the response was markedly different than for F2 lymphocytes. In contrast to F2 lymphocytes, F4 lymphocytes from donors afflicted with cancer had a significant SCM response to PHA, but the equivalent fraction of lymphocytes from donors free of cancer had no response to pHA. In addition, F4 cells exhibited no response to cancer-associated antigen regardless of the donor's condition. It should be noted that the response of the F4 lymphocytes of PHA was the opposite to the response of F2 cells to PHA. Although the reason for this is not understood, F4 lymphocytes can be used in the SCM test to screen blood samples for the presence of cancer A positive SCM response by a donor's F4 lymphocytes provides a positive indication of the presence of a malignancy, calling for further testing and diagnosis.

TABLE 2

SCM RESPONSE OF LYMPHOCYTE FRACTIONS OF EXAMPLE 2 TO PHA AND CANCER ASSOCIATED ANTIGEN (CAA) AS PERCENTAGE OF CONTROL (EXAMPLE 6)

| Fraction No. | PHA$^a$ | CAA$^a$ | PHA$^b$ | CAA$^b$ |
|---|---|---|---|---|
| 1 | 99.9 ± 1.5 | 100 ± 2.0 | 100 ± 2.0 | 99.8 ± 1.5 |
| 2 | 71 ± 6.0 | 99 ± 3.0 | 98 ± 2.0 | 74 ± 6.0 |
| 3 | 101 ± 2.0 | 100 ± 2.0 | 100 ± 2.0 | 100 ± 2.0 |
| 4 | 99 ± 2.5 | 100 ± 2.0 | 74 ± 8.0 | 99 ± 3.0 |
| 5 | 100 ± 1.5 | — | 99 ± 2.0 | — |

$^a$Each value is the mean of 30 samples from healthy donors.
$^b$Each value is the mean of 20 samples from donors diagnosed as having a malignant disorder.

These results clearly show that F4 lymphocytes must be separated from F2 lymphocytes prior to stimulation by a challenging agent, particularly if a mitogen such as PHA is used as the challenging agent. The presence of both F2 and F4 cells in the same SCM assay leads to erroneous results, indicating the absence of malignancy when it is in fact present or vice versa The improved separation technique of the present invention clearly separates both classes of cells from each other and from SCM non-responding cells. This prevents the possibility of occurrence of such erroneous results.

EXAMPLE 7

Use of SCM Response to Determine Allocraft Rejection and Tissue Compatibility

F2 lymphocytes separated in accordance with the procedure of Example 2 from the peripheral blood of an organ transplant recipient are used to indicate the onset of allograft rejection crisis. Utilizing the SCM-response technique of Example 6, the separated F2 lymphocytes are incubated with a tissue extract in PBS obtained from tissue of the organ donor. Organ rejection is indicated when the F2 lymphocytes from the organ recipient show a decrease in intracellular fluorescein fluorescence polarization after contact with the tissue extract from the organ donor/ Compatibility is indicated by no decrease in the polarization value of the recipient's F2 lymphocytes when the donor's tissue extract is used as a challenging agent in the SCM test.

As an alternative to the use of tissue extract as a challenging agent, the F2 lymphocytes of the recipient are incubated with a cell-free extract or essentially cell-free extract containing about 5% cells) in PBS of F2 lymphocytes from the blood of the organ donor, and the resulting SCM response is measured as in Example 6.

The technique of this Example is also utilized prior to the organ transplant to determine compatibility between the organ donor and the potential organ recipient The procedure of this Example is carried in the relatively short time of 3 to 4 hours and is a timesaving alternative to the conventional mixed lymphocyte reaction procedure. The latter procedure is conventionally used as a measure of compatibility between a donor and a recipient and takes between 48 and 72 hours to obtain results.

EXAMPLE 8

SCM Response to Determine Allergic Reaction

F2 lymphocytes separated according to Example 2 from the peripheral blood of a donor suffering from an allergic reaction are used according to the method of Example 6 to determine the reaction of the donor to particular allergens. The allergens can be pollen extract, dust extract, animal hair extract, grass extracts, food extracts, bee toxins, and the like as are presently used in conventional skin patch tests. An allergic response to a particular antigen is indicated by the method of Example 6 by a decrease in the intracellular fluorescein fluorescence polarization value of the donor's F2 lymphocytes. Such a decrease indicates an SCM response by the F2 lymphocytes to a particular allergen. The use of this method can avoid the necessity for painful and inconvenient skin patch tests.

EXAMPLE 9

SCM Response to Determine Viral or Bacterial Infection

F2 lymphocytes are isolated according to the method of Example 2 from the peripheral blood of a donor afflicted with an unknown viral or bacterial infection. The F2 cells are incubated according to the method of Example 6 with extracts or toxins of viruses or bacteria which are suspected to be the cause of the infection. The F2 lymphocytes respond in the SCM test by a decrease in intracellular fluorescein fluorescence polarization only when incubated with the specific toxin or virus that is present in the body of the donor and not when incubated with any other agents.

The SCM-responding lymphocyte isolation method of the present invention meets the needs previously set forth: rapid isolation of SCM-responding lymphocytes, suitability for use by workers With limited training, lack of a requirement for complex manipulations or special dexterity, and reliable separation of the two subpopulations of SCM-responding lymphocytes without cross-contamination or contamination of either of the fractions with SCM non-responding cells.

Additionally, one embodiment of the method eliminates the need for using iron powder or carbonyl-iron powder in a preliminary step of the isolation procedure, simplifying the procedure and avoiding the use of a reagent with possible toxic or hemolytic effects on the lymphocytes.

The method of the present invention allows the isolation of either the F2 subpopulation or the F4 subpopulation of SCM-responding lymphocytes, or both, from the same gradient. It isolates the SCM-responding lymphocytes as well-defined bands, cleanly separated from other blood components, such as non-SCM-responding lymphocytes The use of this method can improve the reliability of the SCM test and its utility in clinical applications.

Although the present invention has been described in considerable detail with regard to certain preferred versions thereof, other versions are possible. Therefore the spirit and scope of the appended claims should not be limited to the description of the preferred version contained herein.

What is claimed is:

1. A method for isolating the F2 subpopulation of SCM-responding lymphocytes from the total population of peripheral blood lymphocytes comprising the steps of:
   (a) layering a first solution having an osmolality between about 0.270 Osm/kg and about 0.330 Osm/kg at 20° C. and a density ($\rho_1$) determined by the equation $\rho_1 = 1.0572 + 0.063 (X - 0.290)$, where X equals the osmolality of the first solution in Osm/kg, on top of a second solution having the same osmolality as the first solution and a density ($\rho_2$) determined by the equation $\rho_2 = 1.0652 + 0.063 (X - 0.290)$, the volumes of the first and second solutions being sufficient to separate the F2 lymphocytes from other peripheral blood lymphocytes;
   (b) layering a volume of peripheral blood lymphocytes on top of the layered first and second solutions;
   (c) centrifuging the peripheral blood lymphocytes layered on top of the layered first and second solutions such that the F2 lymphocyte subpopulation is concentrated in a visible band between the layered first and second solutions; and
   (d) collecting the visible band to obtain the F2 lymphocyte subpopulation, the collected lymphocytes being substantially free of lymphocytes having buoyant densities greater than about 1.0670 g/cm$^3$ or less than about 1.0590 g/cm$^3$, the buoyant densities being measured at 20° C. in a solution having an osmolality of about 0.315 Osm/kg.

2. A method for isolating both the F2 and F4 lymphocytes from the total population of peripheral blood lymphocytes comprising the steps of:
   (a) layering a first, second, third, and fourth solution having the same osmolality on top of each other to form a four-density solution stack:
      (i) the first solution having an osmolality of between about 0.270 Osm/kg and about 0.330 Osm/kg at 20° C. and a density ($\rho_1$) determined by the equation $\rho_1 = 1.0712 + 0.063 (X - 0.290)$, where X equals the osmolality of the first solution in Osm/kg;

(ii) the second solution having a density ($\rho_2$) determined by the equation $\rho_2 = 1.0673 + 0.063 (X - 0.290)$;

(iii) the third solution having a density ($\rho_3$) determined by the equation $\rho_3 = 1.0652 + 0.063 (X - 0.290)$; and (iv) the fourth solution having a density ($\rho_4$) determined by the equation $\rho_4 = 1.0572 + 0.063 (X - 0.290)$; the first solution being positioned on the bottom of the solution stack, the volumes of the four solutions being sufficient to separate the F2 and F4 lymphocytes from each other and from other peripheral blood lymphocytes;

(b) layering a volume of peripheral blood lymphocytes on top of the solution stack;

(c) centrifuging the peripheral blood lymphocytes layered on top of the four-density solution stack such that the F2 lymphocyte subpopulation is concentrated in a visible band between the third and fourth solutions of the solution stack and the F4 lymphocyte subpopulation is concentrated in a visible band between the first and second solutions of the solution stack;

(d) collecting the visible band between the third and fourth solutions to obtain the F2 lymphocyte subpopulation, the collected lymphocytes being substantially free of lymphocytes having collected lymphocytes being substantially free of lymphocytes having buoyant densities greater than about 1.0670 g/cm$^3$ or less than about 1.0590 g/cm$^3$, the buoyant densities being measured at 20° C. in a solution having an osmolality of about 0.315 Osm/kg; and (e) collecting the visible band between the first and second solutions to obtain the F4 lymphocyte subpopulation, the collected lymphocytes being substantially free of lymphocytes having buoyant densities greater than about 1.0730 g/cm$^3$ or less than about 1.0690 g/cm$^3$, the buoyant densities being measured at 20° C. in a solution having an osmolality of about 0.315 Osm/kg.

3. A method for isolating the F4 subpopulation of SCM-responding lymphocytes from the total population of peripheral blood lymphocytes comprising the steps of:

(a) layering a first solution having a osmolality between about 0.270 Osm/kg and about 0.330 Osm/kg at 20° C. and a density ($\rho_1$) determined by the equation $\rho_1 = 1.0672 + 0.063 (X - 0.290)$, where X equals the osmolality of the first solution in Osm/kg, on top of a second solution having the same osmolality as the first solution and a density ($\rho_2$) determined by the equation $\rho_2 = 1.0712 + 0.063 (X - 0.290)$, the volumes of the first and second solutions being sufficient to separate the F4 lymphocytes from other peripheral blood lymphocytes;

(b) layering a volume of peripheral blood lymphocytes on top of the layered first and second solutions;

(c) centrifuging the peripheral blood lymphocytes layered on top of the layered first and second solutions such that the F4 lymphocyte subpopulation is concentrated in a visible band between the layered first and second solutions; and (d) collecting the visible band to obtain the F4 lymphocyte subpopulation, the collected lymphocytes being substantially free of lymphocytes having buoyant densities greater than about 1.0730 g/cm$^3$ or less than about 1.0690 g/cm$^3$, the buoyant densities being measured at 20° C. in a solution having an osmolality of about 0.315 Osm/kg.

4. The method of claim 1 wherein the osmolality of the first and second solutions is 0.320 Osm/kg, the first solution has a density of 1.0590 g/cm$^3$, and the second solution has a density of 1.0670 g/cm$^3$.

5. The method of claim 2 wherein the osmolality of the solutions forming the four-density solution stack is 0.320 Osm/kg, the first solution has a density of 1.0730 g/cm$^3$, the second solution has a density of 1.0690 g/cm$^3$, the third solution has a density of 1.0670 g/cm$^3$, and the fourth solution has a density of 1.0590 g/cm$^3$.

6. The method of claim 3 wherein the osmolality of the first and second solutions is 0.320 Osm/kg, the first solution has a density of 1.0690 g/cm$^3$, and the second solution has a density of 1.0730 g/cm$^3$.

7. The method of claim 1 or 3 wherein the first and second solutions are solutions of polyvinylpyrrolidone-covered colloidal silica.

8. The method of claim 2 wherein the four solutions are solutions of polyvinylpyrrolidone-covered colloidal silica.

9. The method of claim 1, 2, or 3 further comprising the step of isolating the total population of peripheral blood lymphocytes from a heparinized blood sample by density gradient centrifugation in a medium capable of separating the peripheral blood lymphocytes from other blood components.

10. The method of claim 9 wherein the step of isolating the total population of peripheral blood lymphocytes comprises the steps of:

(i) layering heparinized blood on top of a solution of density 1.077 g/cm$^3$ containing a nonionic synthetic polymer of sucrose with a molecular weight of about 400,000 and sodium diatrizoate, the volume of the solution of density 1 077 g/cm$^3$ being at least as great as the volume of heparinized blood, both solutions being equilibrated to room temperature;

(ii) centrifuging the layered solutions at room temperature at sufficient effective gravitational force and for sufficient time so that the lymphocytes are banded at the interface between the solution of density 1.077 g/cm$^3$ and the heparinized blood; and (iii) collecting the lymphocytes from the interface.

11. A method for testing a blood sample for the presence of a condition or a disease comprising the steps of:

(a) heparinizing the blood sample;

(b) isolating substantially all the peripheral blood lymphocytes from the heparinized blood sample;

(c) isolating separately both the F2 and F4 subpopulations of lymphocytes from the total population of peripheral blood lymphocytes by the steps of:

(i) layering a first, second, third, and fourth solution with the same osmolality on top of each other to form a four-density solution stack:

(A) the first solution having an osmolality between about 0.270 Osm/kg and about 0.330 Osm/kg at 20° C. and a density ($\rho_1$) determined by the equation $\rho_1 = 1.0712 + 0.063 (X - 0.290)$, where X equals the osmolality of the first solution in Osm/kg;

(B) the second solution having a density ($\rho_2$) determined by the equation $\rho_2 = 1.9672 + 0.063 (X - 0.290)$;

(C) the third solution having a density ($\rho_3$) determined by the equation $\rho_3 = 1.0652 + 0.063 (X - 0.290)$; and (D) the fourth solution having a density ($\rho_4$) determined by the equation $\rho_4 = 1.0572 + 0.063 (X - 0.290)$; the first solution being positioned on the bottom of the solution stack, the volumes of the four solutions being sufficient to separate the F2 and F4 lymphocytes from each other and from other peripheral blood lymphocytes;

(ii) layering a volume of peripheral blood lymphocytes on top of the solution stack;

(iii) centrifuging the peripheral blood lymphocytes layered on top of the four-density solution stack such that the F2 lymphocyte subpopulation is concentrated in a visible band between the third and fourth solutions of the solution stack and the F4 lymphocyte subpopulation is concentrated in a visible band between the first and second solutions of the solution stack;

(iv) collecting the visible band between the third and fourth solutions to obtain the F2 lymphocyte subpopulation, the collected lymphocytes being substantially free of lymphocytes having buoyant densities greater than about 1.0670 g/cm$^3$ or less than about 1.0590 g/cm$^3$, the buoyant densities being measured at 20° C. in a solution having an osmolality of about 0.315 Osm/kg; and (v) collecting the visible band between the first and second solutions to obtain the F4 lymphocyte subpopulation, the collected lymphocytes being substantially free of lymphocytes having buoyant densities greater than about 1.0730 g/cm$^3$ or less than about 1.0690 g/cm$^3$, the buoyant densities being measured at 20° C. in a solution having an osmolality of about 0.315 Osm/kg;

(d) washing the isolated subpopulations of lymphocytes;

(e) contacting an aliquot of the washed F2 lymphocyte subpopulation with a substance associated with the condition or disease being tested for;

(f) contacting the washed F4 lymphocyte subpopulation with a mitogen capable of stimulating T-cell lymphocytes;

(g) adding a fluorogenic agent precursor to the aliquot of the washed F2 lymphocyte subpopulation contacted with the substance and to the aliquot of the washed F4 lymphocyte subpopulation contacted with the mitogen;

(h) monitoring the response of the aliquot of the F2 lymphocyte subpopulation contacted with the substance by observing the changes in the structuredness of the cytoplasmic matrix of the lymphocytes of the aliquot as a result of the contact between the lymphocytes and the substance;

(i) monitoring the response of the F4 lymphocyte subpopulation contacted with the mitogen by observing the changes in the structuredness of the cytoplasmic matrix of the lymphocytes as a result of the contact between the lymphocytes and the mitogen; and (j) relating the monitored response of the aliquot of the F2 lymphocyte subpopulation and the F4 lymphocyte subpopulation to the presence or absence of the disease or bodily condition.

12. A method for testing a blood sample for the presence of a condition or a disease comprising the steps of:

(a) heparinizing the blood sample;

(b) isolating substantially all the peripheral blood lymphocytes from the heparinized blood sample;

(c) isolating the F2 subpopulation of lymphocytes from the total population of peripheral blood lymphocytes by the steps of:

(i) layering a first solution having an osmolality of between about 0.270 Osm/kg and about 0.330 Osm/kg at 20° C. and a density ($\rho_1$) determined by the equation $\rho_1 = 1.0572 + 0.063 (X - 0.290)$, where X equals the osmolality of the first solution in Osm/kg, on top of a second solution having the same osmolality as the first solution and a density ($\rho_2$) that is determined by the equation $\rho_2 = 1.0652 + 0.063 (X - 0.290)$, the volumes of the first and second solutions being sufficient to separate the F2 lymphocytes from other peripheral blood lymphocytes;

(ii) layering a volume of peripheral blood lymphocytes on top of the layered first and second solutions;

(iii) centrifuging the peripheral blood lymphocytes layered on top of the layered first and second solutions such that the F2 lymphocyte subpopulations is concentrated in a visible band between the layered first and second solutions; and (iv) collecting the visible band to obtain the F2 lymphocyte subpopulation, the collected lymphocytes being substantially free of lymphocytes having buoyant densities greater than about 1.0670 g/cm$^3$ or less than about 1.0590 g/cm$^3$, the buoyant densities being measured at 20° C. in a solution having an osmolality of about 0.315 Osm/kg;

(d) washing the isolated F2 subpopulation of lymphocytes;

(e) contacting an aliquot of the washed F2 lymphocyte subpopulation with a substance associated with the condition or disease being tested for;

(f) adding a fluorogenic agent precursor to the aliquot of the washed F2 lymphocyte subpopulation contacted with the substance;

(g) monitoring the response of the aliquot of the F2 lymphocyte subpopulation contacted with the substance by observing the changes in the structuredness of the cytoplasmic matrix of the lymphocytes of the aliquot as a result of the contact between the lymphocytes and the substance; and (h) relating the monitored response of the aliquot of the F2 lymphocyte subpopulation to the presence or absence of the disease or bodily condition.

13. A method for testing a blood sample from a donor for the presence of cancer in the donor comprising the steps of:

(a) heparinizing the blood sample;

(b) isolating substantially all the peripheral blood lymphocytes from the heparinized blood sample;

(c) isolating the F4 subpopulation of lymphocytes from the total population of peripheral blood lymphocytes by the steps of:

(i) layering a first solution having a osmolality between about 0.270 Osm/kg and about 0.330 Osm/kg at 20° C. and a density ($\rho_1$) determined by the equation $\rho_1 = 1.672 + 0.063 (X - 0.290)$, where X equals the osmolality of the first solution in Osm/kg, on top of a second solution having the same osmolality as the first solution and a density ($\rho_2$) determined by the equation $\rho_1 = 1.0712 + 0.063 \, (X - 0.290)$, the volumes of the first and second solutions being sufficient to separate the F4 lymphocytes from other peripheral blood lymphocytes;

(ii) layering a volume of peripheral blood lymphocytes on top of the layered first and second solutions;

(iii) centrifuging the peripheral blood lymphocytes layered on top of the layered first and second solutions such that the F4 lymphocyte subpopulation is concentrated in a visible band between the layered first and second solutions; and (iv) collecting the visible band to obtain the F4 lymphocyte subpopulation, the collected lymphocytes being substantially free of lymphocytes having buoyant densities greater than about 1.0730 g/cm$^3$ or less than about 1.0690 g/cm$^3$, the buoyant densities being measured at 20° C. in a solution having an osmolality of about 0.315 Osm/kg;

(d) washing the isolated F4 subpopulation of lymphocytes;

(e) contacting the washed F4 lymphocyte subpopulation with the mitogen;

(f) adding a fluorogenic agent precursor to the aliquot of the washed F4 lymphocyte subpopulation contacted with the mitogen;

(g) monitoring the response of the F4 lymphocyte subpopulation contacted with the mitogen by observing the changes in the structuredness of the cytoplasmic matrix of the lymphocytes of the aliquot as a result of the contact between the lymphocytes and the mitogen; and (h) relating the monitored response of the F4 lymphocyte subpopulation to the presence or absence of cancer.

14. The method of claim 11 or claim 12 wherein the condition or disease associated substance is a cancer associated substance.

15. The method of claim 11 wherein the condition or disease associated substance is selected from the group consisting of viral associated antigens and bacterial associated antigens.

16. The method of claim 11 wherein the condition or disease associated substance is capable of causing a decrease in the structuredness of the cytoplasmic matrix of lymphocytes incompatible with the donor of the lymphocytes producing the substance and is present as an indicator of allograft rejection crisis.

17. The method of claim 11 wherein the substance is tissue extract from a transplant donor and the step of relating the monitored response comprises determining compatibility for organ transplantation between a transplant recipient, from which the blood sample was obtained, and the transplant donor, from whom the tissue extract was obtained.

18. The method of claim 11 comprising the additional steps of:

(a) also contacting a second aliquot of the washed F2 lymphocyte subpopulation with the mitogen capable of stimulating T-cell lymphocytes;

(b) adding a fluorogenic agent precursor to the second aliquot of the washed F2 lymphocyte subpopulation contacted with the mitogen;

(c) monitoring the response of the mitogen-contacted second aliquot of the F2 lymphocyte subpopulation by observing the changes in the structuredness of the cytoplasmic matrix of the lymphocytes of the aliquot as a result of the contact between the lymphocytes and the mitogen: and (d) relating the monitored response of the second aliquot of the F2 lymphocyte subpopulation to the presence or absence of the disease or bodily condition to confirm the result obtained with the first aliquot of the F2 lymphocyte subpopulation and with the F4 lymphocyte subpopulation.

19. The method of claim 12 comprising the additional steps of:

(a) further contacting a second aliquot of the washed F2 lymphocyte subpopulation with a mitogen capable of stimulating T-cell lymphocytes;

(b) adding a fluorogenic agent precursor to the second aliquot of the washed F2 lymphocyte subpopulation contacted with the mitogen;

(c) monitoring the response of the mitogen-contacted second aliquot of the F2 lymphocyte subpopulation to the mitogen by observing the changes in the structuredness of the cytoplasmic matrix of the lymphocytes of the second aliquot as a result of the contact between the lymphocytes and the mitogen; and (d) relating the monitored response of the second aliquot of the F2 lymphocyte subpopulation to the presence or absence of the disease or bodily condition to confirm the result obtained with the first aliquot of the F2 lymphocyte subpopulation.

20. The method of claim 11, 13, 18, or 19 wherein the mitogen is reagent grade phytohaemagglutinin.

21. The method of claim 11 wherein the osmolality of the solutions forming the four-density solution stack is 0.320 Osm/kg, the first solution has a density of 1.0730 g/cm$^3$, the second solution has a density of 1.0690 g/cm$^3$, the third solution has a density of 1.0670 g/cm$^3$, and the fourth solution has a density of 1.0590 g/cm$^3$.

22. The method of claim 12 wherein the osmolality of the first and second solutions is 0.320 Osm/kg, the first solution has a density of 1.0590 g/cm$^3$, and the second solution has a density of 1.0670 g/cm$^3$.

23. The method of claim 13 wherein the osmolality of the first and second solutions is 0.320 Osm/kg, the first solution has a density of 1.0690 g/cm$^3$, and the second solution has a density of 1.0730 g/cm$^3$.

24. The method of claim 11, 12, or 13 wherein the step of isolating substantially all the peripheral blood lymphocytes from the heparinized blood sample comprises the steps of:

(i) layering heparinized blood on top of a solution of density 1.077 g/cm$^3$ containing a nonionic synthetic polymer of sucrose with a molecular weight of about 400,000 and sodium diatrizoate, the volume of the solution of density 1,077 g/cm, being at least as great as the volume of heparinized blood, both solutions being equilibrated to room temperature;

(ii) centrifuging the layered solutions at room temperature at sufficient effective gravitational force and for sufficient time so that the lymphocytes are banded at the interface between the solution of density 1.077 g/cm$^3$ and the heparinized blood; and (iii) collecting the lymphocytes from the interface.

25. The method of claim 11 wherein the four solutions are solutions of polyvinylpyrrolidone-covered colloidal silica.

26. The method of claim 12 or 13 wherein the first and second solutions are solutions of polyvinylpyrrolidone-covered colloidal silica.

27. A method for isolating the F2 subpopulation of SCM-responding lymphocytes from a heparinized blood sample, comprising the steps of:
   (a) removing the phagocytic cells from the heparinized blood sample; and
   (b) isolating the F2 subpopulation of lymphocytes from the blood sample depleted of phagocytic cells by the steps of:
      (i) layering a first solution having a osmolality between about 0.270 Osm/kg and about 0.330 Osm/kg at 20° C. and a density ($\rho_1$) determined by the equation $\rho_1 = 1.0572 + 0.063 \, (X - 0.290)$, where X equals the osmolality of the first solution in Osm/kg, on top of a second solution having the same osmolality as the first solution and a density $\rho_2$) that is determined by the equation $\rho_2 = 1.0652 + 0.0623 \, (X - 0.290)$, the volumes of the first and second solutions being sufficient to separate the F2 lymphocytes from other lymphocytes present in the blood sample depleted of phagocytic cells;
      (ii) layering a volume of the blood sample depleted of phagocytic cells on top of the layered first and second solutions;
      (iii) centrifuging the blood sample depleted of phagocytic cells layered on top of the layered first and second solutions such that the F2 lymphocyte subpopulation is concentrated in a visible band between the layered first and second solutions; and
      (iv) collecting the visible band to obtain the F2 lymphocyte subpopulation, the collected lymphocytes being substantially free of lymphocytes having buoyant densities greater than about 1.0670 g/cm$^3$ or less than about 1.0590 g/cm$^3$, the buoyant densities being measured at 20° C. in a solution having an osmolality of about 0.315 Osm/kg.

28. A method for separately isolating both the F2 and F4 subpopulation of SCM-responding lymphocytes from a heparinized blood sample, comprising the steps of:
   (a) removing the phagocytic cells from the heparinized blood sample; and
   (b) isolating separately both the F2 and F4 subpopulation of lymphocytes by the steps of:
      (i) layering a first, second, third, and fourth solution having the same osmolality on top of each other to form a four-density solution stack:
         (A) the first solution having an osmolality between about 0.270 Osm/kg and about 0.330 Osm/kg at 20° C. and a density ($\rho_1$) determined by the equation $\rho_1 = 1.0712 + 0.063 \, (X - 0.290)$, where X equals the osmolality of the first solution in Osm/kg;
         (B) the second solution having a density ($\rho_2$) determined by the equation $\rho_2 = 1.0672 + 0.063 \, (X - 0.290)$;
         (C) the third solution having a density ($\rho_3$) determined by the equation $\rho_3 = 1.0652 + 0.063 \, (X - 0.290)$; and
         (D) the fourth solution having a density ($\rho_4$) determined by the equation $\rho_4 = 1.0572 + 0.063 \, (X - 0.290)$; the first solution being positioned on the bottom of the solution stack, the volumes of the four solutions being sufficient to separate the F2 and F4 lymphocytes from each other and from other lymphocytes present in the blood sample depleted of phagocytic cells;
      (ii) layering a volume of the blood sample depleted of phagocytic cells on top of the solution stack;
      (iii) centrifuging the blood sample depleted of phagocytic cells layered on top of the four-density solution stack such that the F2 lymphocyte subpopulation is concentrated in a visible band between the third and fourth solutions of the solution stack and the F4 lymphocyte subpopulation is concentrated in a visible band between the first and second solutions of the solution stack;
      (iv) collecting the visible band between the third and fourth solutions to obtain the F2 lymphocyte subpopulation, the collected lymphocytes being substantially free of lymphocytes having buoyant densities greater than about 1.0670 g/cm$^3$ or less than about 1.0590 g/cm$^3$, the buoyant densities being measured at 20° C. in a solution having an osmolality of about 0.315 Osm/kg; and
      (v) collecting the visible band between the first and second solutions to obtain the F4 lymphocyte subpopulation, the collected lymphocytes being substantially free of lymphocytes having buoyant densities greater than about 1.0730 g/cm$^3$ or less than about 1.0690 g/cm$^3$, the buoyant densities being measured at 20° C. in a solution having an osmolality of about 0.315 Osm/kg.

29. A method for isolating the F4 subpopulation of SCM-responding lymphocytes from a heparinized blood sample, comprising the steps of:
   (a) removing the phagocytic cells from the heparinized blood sample; and
   (b) isolating the F4 subpopulation of lymphocytes from the blood sample depleted of phagocytic cells by the steps of:
      (i) layering a first solution having an osmolality between about 0.270 Osm/kg and about 0.330 Osm/kg at 20° C. and a density ($\rho_1$) determined by the equation $\rho_1 = 1.0672 + 0.063 \, (X - 0.290)$, where X equals the osmolality of the first solution in Osm/kg, on top of a second solution having the same osmolality as the first solution and a density ($\rho_2$) that is determined by the equation $\rho_2 = 1.0712 + 0.063 \, (X - 0.290)$, the volumes of the first and second solutions being sufficient to separate the F4 lymphocytes from other lymphocytes present in the blood sample depleted of phagocytic cells;
      (ii) layering a volume of the blood sample depleted of phagocytic cells on top of the layered first and second solutions;
      (iii) centrifuging the blood sample depleted of phagocytic cells layered on top of the layered first and second solutions such that the F4 lymphocyte subpopulation is concentrated in a visible band between the layered first and second solutions; and
      (iv) collecting the visible band to obtain the F4 lymphocyte subpopulation, the collected lymphocytes being substantially free of lymphocytes having buoyant densities greater than about 1.0730 g/cm$^3$ or less than about 1.0690 g/cm$^3$, the buoyant densities being measured at 20° C. in a solution having an osmolality of about 0.315 Osm/kg.

30. A method for testing a blood sample for the presence of a condition or a disease comprising the steps of:

(a) isolating from the blood sample two discrete fractions of lymphocytes, and F2 fraction containing lymphocytes having buoyant densities of from about 1.0590 g/cm$^3$ to about 1.0670 g/cm$^3$ and an F4 fraction having buoyant densities of from about 1.0690 g/cm$^3$ to about 1.0730 g/cm$^3$, each fraction being substantially free of lymphocytes having buoyant densities other than those defining the fraction, the buoyant densities being measured at 20° C. in a solution having an osmolality of about 0.315 Osm/kg;

(b) washing the isolated fractions of lymphocytes;

(c) contacting an aliquot of the isolated washed F2 fraction with a substance associated with the condition or disease being tested for;

(d) contacting the isolated washed F4 fraction with a mitogen capable of stimulating T-cell lymphocytes;

(e) adding a fluorogenic agent precursor to the aliquot of the washed F2 lymphocyte subpopulation contacted with the substance and to the aliquot of the washed F4 lymphocyte subpopulation contacted with the mitogen;

(f) monitoring the response of the aliquot of the F2 fraction contacted with the substance by observing the changes in the structuredness of the cytoplasmic matrix of the lymphocytes of the aliquot as a result of the contact between the lymphocytes and the substance;

(g) monitoring the response of the F4 fraction contacted with the substance by observing the changes in the structuredness of the cytoplasmic matrix of the lymphocytes of the fraction as a result of the contact between the lymphocytes and the mitogen; and (h) relating the monitored responses of the aliquot of the F2 fraction and of the F4 fraction to the presence or absence of the disease or bodily condition.

31. The method of claim 30 wherein the condition or disease associated substance is a cancer associated substance.

32. The method of claim 30 wherein the condition or disease associated substance is selected from the group consisting of viral associated antigens and bacterial associated antigens.

33. The method of claim 30 wherein the condition or disease associated substance is capable of causing a decrease in the structuredness of the cytoplasmic matrix of lymphocytes incompatible with the donor of the lymphocytes producing the substance and is present as an indicator of allograft rejection crisis.

34. The method of claim 30 wherein the substance is tissue extract from a transplant donor and the step of relating the monitored response comprises determining compatibility for organ transplantation between a transplant recipient, from which the blood sample was obtained, and the transplant donor, from which the tissue extract was obtained.

35. The method of claim 30 wherein the step of isolating the two discrete fractions of lymphocytes comprises the steps of:

(i) centrifuging a solution at a sufficient effective gravitational force to preform a multi-density gradient having a minimum density of no greater than about 1.050 g/cm$^3$ and a maximum density of no less than about 1.080 g/cm$^3$; and (ii) centrifuging the blood sample in the preformed gradient.

36. The method of claim 30 wherein the step of isolating the two discrete fractions of lymphocytes comprises centrifuging the blood sample in a multi-density gradient solution produced by layering at least two fluids of different density and equal osmolality such that a less dense fluid is layered on top of a more dense fluid, the maximum density of the gradient being the density of the most dense fluid and the minimum density of the gradient being the density of the least dense fluid.

37. The method of claim 30 comprising the additional steps of:

(a) further contacting a second aliquot of the isolated washed F2 fraction with the mitogen capable of stimulating T-cell lymphocytes;

(b) adding a fluorogenic agent precursor to the second aliquot of the washed F2 lymphocyte subpopulation contacted with the mitogen;

(c) monitoring the response of the mitogen-contacted second aliquot of the F2 lymphocyte subpopulation to the mitogen by observing the changes in the structuredness of the cytoplasmic matrix of the lymphocytes in the second aliquot of the fraction as a result of the contact between the lymphocytes and the mitogen; and (d) relating the monitored response of the second aliquot of the F2 fraction to the presence or absence of the disease or bodily condition to confirm the result obtained with the first aliquot of the F2 fraction and with the F4 lymphocyte subpopulation.

38. The method of claim 37 wherein the mitogen is reagent grade phytohaemagglutinin.

39. A method for classifying and separating from a blood sample lymphocytes capable of responding to stimulation by (i) a substance associated with a disease or condition or (ii) a mitogen capable of stimulating T-cell lymphocytes comprising the steps of:

(a) forming a multi-density gradient solution having a minimum density of no greater than about 1.050 g/cm$^3$ and a maximum density of no less than about 1.080 g/cm$^3$ at 20° C.;

(b) layering the blood sample on top of the multi-density gradient solution;

(c) centrifuging the blood sample in the multi-density gradient solution at a controlled temperature and at sufficient effective gravitational force to cause components of the blood sample to separate and be distributed and retained in the multi-density gradient solution according to the buoyant densities of the blood components;

(d) separating aliquots of the multi-density gradient solution, including the retained blood components in each aliquot, according to the density of the aliquots;

(e) collecting at least two aliquots of the multi-density gradient solution in discrete fractions, the aliquots containing the portions of the multi-density gradient solution having densities respectively of from about 1.0590 g/cm$^3$ to about 1.0670 g/cm$^3$ and from about 1.0690 g/cm$^3$ to about 1.0730 g/cm$^3$; and (f) separately washing the two aliquots to obtain two suspensions of lymphocytes, the lymphocytes in at least one of the suspensions being capable of responding to stimulation by either the condition or disease associated substance or the mitogen, each suspension being substantially free of lymphocytes having buoyant densities other than those defining the collected aliquots.

40. The method of claim 39 wherein the multi-density gradient solution comprises a continuous density gradient.

41. The method of claim 39 wherein the multi-density gradient solution has an osmolality of about 0.315 to 0.320 Osm/kg.

42. The method of claim 39 wherein the blood sample is centrifuged at about 550 g at a temperature of 20° C. in the multi-density gradient solution.

43. The method of claim 39 wherein the multi-density gradient solution comprises an aqueous solution of colloidal silica diluted with saline solution.

44. The method of claim 43 wherein the colloidal silica is coated with an inert material.

45. The method of claim 39 wherein the multi-density gradient solution is produced by layering at least two fluids of different density and equal osmolality such that a less dense fluid is layered on top of a more dense fluid, the maximum density of the gradient being the density of the most dense fluid and the minimum density of the gradient being the density of the least dense fluid.

46. The method of claim 39 wherein the mitogen is reagent grade phytohaemagglutinin.

47. A method for testing a blood sample for the presence of a condition or a disease based upon the response of lymphocytes separated from a blood sample to contact with a substance associated with the condition or disease being tested for comprising the steps of:
  (a) isolating from the blood sample a discrete F2 fraction of lymphocytes containing lymphocytes having buoyant densities of from about 1.0590 g/cm$^3$ to about 1.0670 g/cm$^3$, the fraction being substantially free of lymphocytes having buoyant densities other than those defining the fraction, with the buoyant densities being measured at 20° C. in a solution having an osmolality of about 0.315 Osm/kg;
  (b) washing the isolated fraction of F2 lymphocytes;
  (c) contacting an aliquot of the isolated washed F2 fraction with a substance associated with the condition or disease being tested for;
  (d) adding a fluorogenic agent precursor to the aliquot of the washed F2 lymphocyte subpopulation contacted with the substance;
  (e) monitoring the response of the aliquot of the F2 fraction contacted with the substance by observing the changes in the structuredness of the cytoplasmic matrix of the lymphocytes of the aliquot as a result of the contact between the lymphocytes and the substance; and
  (f) relating to the monitored response of the aliquot of the F2 fraction to the presence or absence of the disease or bodily condition.

48. The method of claim 47 wherein the step of isolating the discrete F2 fraction of lymphocytes comprises:
  (i) centrifuging a solution at a sufficient effective gravitational force to preform a multi-density gradient having a minimum density of no greater than about 1.050 g/cm$^3$ and a maximum density of no less than about 1.070 g/cm$^3$; and
  (ii) centrifuging the blood sample in the preformed gradient.

49. The method of claim 47 wherein the step of isolating the fraction of lymphocytes comprises centrifuging the blood sample in a multi-density gradient solution produced by layering at least two fluids of different density and equal osmolality such that a less dense fluid is layered on top of a more dense fluid, the maximum density of the gradient being the density of the most dense fluid and the minimum density of the gradient being the density of the least dense fluid.

50. The method of claim 47 comprising the additional steps of:
  (a) further contacting a second aliquot of the isolated washed F2 fraction with the mitogen capable of stimulating T-cell lymphocytes;
  (b) adding a fluorogenic agent precursor to the second aliquot of the washed F2 lymphocyte subpopulation contacted with the mitogen;
  (c) monitoring the response of the mitogen-contacted second aliquot of the F2 lymphocyte subpopulation to the mitogen by observing the changes in the structuredness of the cytoplasmic matrix of the lymphocytes in the second aliquot of the fraction as a result of the contact between the lymphocytes and the mitogen; and
  (d) relating the monitored response of the second aliquot of the F2 fraction to the presence or absence of the disease or bodily condition to confirm the result obtained with the first aliquot of the F2 fraction.

51. The method of claim 50 wherein the mitogen is reagent grade phytohaemagglutinin.

52. The method of claim 47 wherein the condition or disease associated substance is a cancer-associated substance.

53. The method of claim 47 wherein the condition or disease associated substance is selected from the group consisting of viral associated antigens and bacterial associated antigens.

54. The method of claim 47 wherein the condition or disease associated substance is capable of causing a decrease in the structuredness of the cytoplasmic matrix of lymphocytes incompatible with the donor of the lymphocytes producing the substance and is present as an indicator of allograft rejection crisis.

55. The method of claim 47 wherein the substance is tissue extract from a transplant donor and the step of relating the monitored response comprises determining compatibility for organ transplantation between a transplant recipient, from which the blood sample was obtained, and the transplant donor, from which the tissue extract was obtained.

56. A method for classifying and separating from a blood sample lymphocytes capable of responding to stimulation by (i) a substance associated with a disease or condition or (ii) a mitogen capable of stimulating T-cell lymphocytes, comprising the steps of:
  (a) forming a multi-density gradient solution having a minimum density of no greater than about 1.050 g/cm$^3$ and a maximum density of no less than about 1.070 g/cm$^3$ at 20° C.;
  (b) layering the blood sample on top of the multi-density gradient solution;
  (c) centrifuging the blood in the multi-density gradient solution at a controlled temperature and at sufficient effective gravitational force to cause components of the blood sample to separate and be distributed and retained in the multi-density gradient solution according to the buoyant densities of the blood components;
  (d) separating aliquots of the multi-density gradient solution, including the retained blood components in each aliquot, according to the density of the aliquots;

(e) collecting an aliquot of the multi-density gradient solution in a discrete fraction, the aliquot containing the portion of the multi-density gradient having densities of from about 1.0590 g/cm$^3$ to about 1.0670 g/cm$^3$; and (f) washing the aliquot to obtain a suspension of lymphocytes, the lymphocytes being capable of responding to stimulation by either the condition or disease associated substance or the mitogen, the suspension being substantially free of lymphocytes having buoyant densities other than those defining the collected aliquot.

57. The method of claim 56 wherein the multi-density gradient solution comprises a continuous density gradient.

58. The method of claim 56 wherein the multi-density gradient solution has an osmolality of about 0.315 to about 0.320 Osm/kg.

59. The method of claim 56 wherein the blood sample is centrifuged at about 550 g at a temperature of 20° C. in the multi-density gradient solution.

60. The method of claim 56 wherein the multi-density gradient solution comprises an aqueous solution of colloidal silica diluted with saline solution.

61. The method of claim 56 wherein the colloidal silica is coated with an inert material.

62. The method of claim 56 wherein the multi-density gradient solution is produced by layering at least two fluids of different density and equal osmolality such that a less dense fluid is layered on top of a more dense fluid, the maximum density of the gradient being the density of the most dense fluid and the minimum density of the gradient being the density of the least dense fluid.

63. The method of claim 56 wherein the mitogen is reagent grade phytohaemagglutinin.

64. A method for treating a blood sample from a donor for the presence of cancer in the donor based upon the response of lymphocytes separated from a blood sample with a mitogen capable of stimulating T-cell lymphocytes comprising the steps of:

(a) isolating from the blood sample a discrete F4 fraction of lymphocytes containing lymphocytes having buoyant densities of about 1.0690 g/cm$^3$ to about 1.0730 g/cm$^3$, the fraction being substantially free of lymphocytes having buoyant densities other than those defining the fraction, with the buoyant densities being measured at 20° C. in a multi-density gradient solution having an osmolality of about 0.315 Osm/kg;

(b) washing the isolated fraction;

(c) contacting the washed F4 fraction with the mitogen;

(d) adding a fluorogenic agent precursor to the washed F4 fraction contacted with the mitogen;

(e) monitoring the response of the F4 fraction contacted with the substance by observing the changes in the structuredness of the cytoplasmic matrix of the lymphocytes as a result of the contact between the lymphocytes and the substance; and (f) relating to the monitored response of the F4 fraction to the presence or absence of cancer.

65. The method of claim 64 wherein the step of isolating the discrete F4 fraction of lymphocytes comprises:

(i) centrifuging a solution at a sufficient effective gravitational force to preform a multi-density gradient having a minimum density of no greater than about 1.060 g/cm$^3$ and a maximum density of no less than about 1.080 g/cm$^3$; and (ii) centrifuging the blood sample in the preformed gradient.

66. The method of claim 64 wherein the step of isolating the discrete F4 fraction of lymphocytes comprises centrifuging the blood sample in a multi-density gradient solution produced by layering at least two fluids of different density and equal osmolality such that a less dense fluid is layered on top of a more dense fluid, the maximum density of the gradient being the density of the most dense fluid and the minimum density of the gradient being the density of the least dense fluid.

67. The method of claim 64 wherein the mitogen is reagent grade phytohaemagglutinin.

68. A method for classifying and separating from a blood sample lymphocytes capable of responding to stimulation by a mitogen capable of stimulating T-cell lymphocytes, the response being exhibited by measurable changes in the structuredness of the cytoplasmic matrix, i.e., decrease in the intracellular fluorescence polarization, of the lymphocytes in response to contact between the lymphocytes and the mitogen, the method comprising the steps of:

(a) forming a multi-density gradient solution having a minimum density of no greater than about 1.060 g/cm$^3$ and a maximum density of no less than about 1.080 g/cm$^3$;

(b) layering the blood sample on top of the multi-density gradient solution;

(c) centrifuging the blood in the multi-density gradient solution at a controlled temperature and at sufficient effective gravitational force to cause components of the blood sample to separate and be distributed and retained in the multi-density gradient solution according to the buoyant density of the blood components;

(d) separating aliquots of the multi-density gradient solution, including the retained blood components in each aliquot, according to the density of the aliquots;

(e) collecting an aliquot of the multi-density gradient solution in a discrete fraction, the aliquot containing the portion of the multi-density gradient having densities of about 1.0690 g/cm$^3$ to about 1.0730 g/cm$^3$; and (f) washing the aliquot to obtain a suspension of lymphocytes, the suspension being substantially free of lymphocytes having buoyant densities other than those defining the collected aliquot.

69. The method of claim 68 wherein the multi-density gradient solution comprises a continuous density gradient.

70. The method of claim 68 wherein the multi-density gradient solution has an osmolality of about 0.315 to about 0.320 Osm/kg.

71. The method of claim 68 wherein the blood sample is centrifuged at about 550 g at a temperature of 20° C. in the multi-density gradient solution.

72. The method of claim 68 wherein the multi-density gradient solution comprises an aqueous solution of colloidal silica diluted with saline solution.

73. The method of claim 72 wherein the colloidal silica is coated with an inert material.

74. The method of claim 73 wherein the multi-density gradient solution is produced by layering at least two fluids of different density and equal osmolality such that a less dense fluid is layered on top of a more dense fluid, the maximum density of the gradient being the density of the most dense fluid and the minimum density of the gradient being the density of the least dense fluid.

75. The method of claim 68 wherein the mitogen is reagent grade phytohaemagglutinin.

76. The method of claim 27 wherein the phagocytic cells are removed from the heparinized blood sample by incubation of the blood sample with a powdered magnetic substance selected from the group consisting of carbonyl-iron powder and iron powder, followed by separation of the phagocytic cells from the remainder of the blood sample by application of magnetic force.

77. The method of claim 28 wherein the phagocytic cells are removed from the heparinized blood sample by incubation of the blood sample with a powdered magnetic substance selected from the group consisting of carbonyl-iron powder and iron powder, followed by separation of the phagocytic cells from the remainder of the blood sample by application of magnetic force.

78. The method of claim 29 wherein the phagocytic cells are removed from the heparinized blood sample by incubation of the blood sample with a powdered magnetic substance selected from the group consisting of carbonyl-iron powder and iron powder, followed by separation of the phagocytic cells from the remainder of the blood sample by application of magnetic force.

79. The method of claim 12 wherein the condition or disease associated substance is selected from the group consisting of viral associated antigens and bacterial associated antigens.

80. The method of claim 12 wherein the condition or disease associated substance is capable of causing a decrease in the structuredness of the cytoplasmic matrix of lymphocytes incompatible with the donor of the lymphocytes producing the substance and is present as an indicator of allograft rejection crisis.

81. The method of claim 12 wherein the substance is tissue extract from a transplant donor and the step of relating the monitored response comprises determining compatibility for organ transplantation between a transplant recipient, from whom the blood sample was obtained, and the transplant donor, from whom the tissue extract was obtained.

* * * * *